United States Patent

Cross et al.

[11] Patent Number: 5,744,488
[45] Date of Patent: Apr. 28, 1998

[54] INDOLE DERIVATIVES THROMBOXANE A2 ANTAGONISTS

[75] Inventors: Peter Edward Cross; Kevin Neil Dack; Roger Peter Dickinson; John Steele, all of Sandwich, United Kingdom

[73] Assignee: Pfizer Inc., New York, N.Y.

[21] Appl. No.: 601,013

[22] PCT Filed: Aug. 9, 1994

[86] PCT No.: PCT/EP94/02660

§ 371 Date: Feb. 23, 1996

§ 102(e) Date: Feb. 23, 1996

[87] PCT Pub. No.: WO95/06046

PCT Pub. Date: Mar. 2, 1995

[30] Foreign Application Priority Data

Aug. 26, 1993 [GB] United Kingdom ............... 9317764

[51] Int. Cl.⁶ .................... A61K 31/44; C07D 401/06
[52] U.S. Cl. .................... 514/339; 514/397; 514/415; 546/277.4; 548/503; 548/483; 548/312.1
[58] Field of Search ................. 546/277.4; 548/312.1, 548/503, 483; 514/339, 397, 415

[56] References Cited

U.S. PATENT DOCUMENTS 4,474,967  10/1984  Sarges ..................... 548/309

FOREIGN PATENT DOCUMENTS 0073663  3/1983  European Pat. Off.
2045244  10/1980  United Kingdom.

OTHER PUBLICATIONS

R. B. Silverman, in "The Synthesis of Radioactive Compounds," *The Organic Chemistry of Drug Design and Drug Action*, Academic Press, a division of Harcourt Broce & Company, San Diego, California, 1992, pp. 279–284.

*Primary Examiner*—Jane Fan
*Attorney, Agent, or Firm*—Peter C. Richardson; Paul H. Ginsburg; Garth Butterfield

[57] ABSTRACT

Compounds of formula (I):

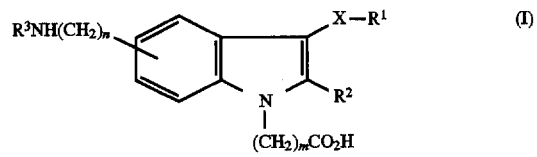

and pharmaceutically acceptable salt and biolabile esters thereof, wherein $R^1$ is H, $C_1$–$C_4$ alkyl, phenyl optionally substituted by up to three substituents independently selected from $C_1$–$C_4$ alkyl, $C_1$–$C_4$ alkoxy, halogen and $CF_3$, or is 1-imidazolyl, 3-pyridyl or 4-pyridyl; $R^2$ is H or $C_1$–$C_4$ alkyl, $R^3$ is $SO_2R^4$ or $COR^4$ where $R^4$ is $C_1$–$C_6$ alkyl, $C_1$–$C_3$ perfluoroalkyl$(CH_2)_p$, $C_3$–$C_6$ cycloalkyl$(CH_2)_p$, aryl$(CH_2)_p$, or heteroaryl$(CH_2)_p$, p being 0, 1 or 2, or $R^4$ may be $NR^5R^6$ where $R^5$ is H or $C_1$–$C_4$ alkyl and $R^6$ is $C_1$–$C_6$, alkyl, $C_3$–$C_6$ cycloalkyl or aryl, or $R^5$ and $R^6$ together with the nitrogen atom to which they are attached form a 5- to 7-membered heterocyclic ring which may optionally incorporate a carbon-carbon double bond or a further heteroatom linkage selected from O, S, NH, N($C_1$–$C_4$ alkyl) and N($C_1$–$C_5$ alkanoyl); X is $CH_2$ or a direct link, with the proviso that when $R^1$ is 1-imidazolyl then X is $CH_2$; m is 2, or 3; n is 0, 1 or 2, and wherein the group $(CH_2)_nNHR^3$ is attached at the 5-position when n is 0 or 1, or at the 5- or 4-position when n is 2. These compounds are selective $TXA_2$ and $PGH_2$ antagonists. Some also inhibit thromboxane synthetase.

9 Claims, No Drawings

INDOLE DERIVATIVES THROMBOXANE A2 ANTAGONISTS

BACKGROUND OF THE INVENTION

This invention relates to certain indole alkanoic acids. Such compounds are able to selectively antagonise the effect of thromboxane $A_2$ ($TXA_2$), and its precursor prostaglandin $H_2$ ($PGH_2$), at the thromboxane receptor. In addition, certain of the compounds also selectively inhibit the thromboxane synthetase enzyme. The compounds are thus useful as therapeutic agents and they may be used either alone, or, in the case of compounds which do not inhibit the thromboxane synthetase enzyme, preferably in combination with a thromboxane synthetase inhibitor, for example in the treatment of atherosclerosis and unstable angina and for prevention of reocculsion, both acute and chronic, after percutaneous transluminal coronary and femoral angioplasty. The compounds may also find clinical utility in a further variety of disease conditions in which thromboxane $A_2$ has been implicated such as in the treatment of myocardial infarction, stroke, cardiac arrhythmias, transient isohaemic attack, tumour metastasis, peripheral vascular disease, bronchial asthma, renal disease, cyclosporin-induced neprotoxicity, renal allograft rejection, vascular complications of diabetes and endotoxin shock, trauma, pre-eclampsia and in coronary artery bypass surgery and haemodialysis.

SUMMARY OF THE INVENTION

The compounds of the invention are of formula (I):

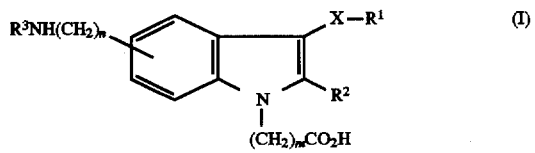

and pharmaceutically acceptable salts and biolabile esters thereof, wherein $R^1$ is H, $C_1$–$C_4$ alkyl, phenyl optionally substituted by up to three substituents independently selected from $C_1$–$C_4$ alkyl, $C_1$–$C_4$ alkoxy, halogen and $CF_3$, or is 1-imidazolyl, 3-pyridyl or 4-pyridyl;

$R^2$ is H or $C_1$–$C_4$ alkyl, $R^3$ is $SO_2R^4$ or $COR^4$ where $R^4$ is $C_1$–$C_6$ alkyl, $C_1$–$C_3$ perfluoralkyl$(CH_2)_p$, $C_3$–$C_6$ cycloalkyl$(CH_2)_p$, aryl $(CH_2)_p$ or heteroaryl$(CH_2)_p$, p being 0, 1 or 2, or $R^4$ may be $NR^5R^6$ where $R^5$ is H or $C_1$–$C_4$ alkyl and $R^6$ is $C_1$–$C_6$ alkyl, $C_3$–$C_6$ cycloalkyl or aryl, or $R^5$ and $R^6$ together with the nitrogen atom to which they are attached form a 5- to 7-membered heterocyclic ring which may optionally incorporate a carbon-carbon double bond or a further heteroatom linkage selected from O, S, NH, N($C_1$–$C_4$ alkyl) and N($C_1$–$C_5$ alkanoyl);

X is $CH_2$ or a direct link, with the proviso that when $R^1$ is 1-imidazolyl then X is $CH_2$;

m is 2, or 3;

n is 0, 1 or 2, and wherein the group $(CH_2)_n NHR^3$ is attached at the 5-position when n is 0 or 1, or at the 5- or 4-position when n is 2.

In the above definitions "aryl" means phenyl or naphthyl and "heteroaryl" means furyl, thienyl or pyridyl, any of which ring systems may optionally be substituted with one to three substituents each independently chosen from $C_1$–$C_4$ alkyl, $C_1$–$C_4$ alkoxy, halo, $CF_3$, $OCF_3$ and CN. Alkyl and alkoxy groups having three or more carbon atoms may be straight chain or branched chain. "Halo" means fluoro, chloro, bromo or iodo.

Compounds containing asymmetric centres can exist as enantiomers and diastereisomers, and the invention includes the separated individual isomers as well as mixtures of isomers.

Also included in the invention are radiolabelled derivatives of compounds of formula (I) which are suitable for biological studies.

The term biolabile ester in the above definition means a pharmaceutically acceptable, biologically degradable ester derivative of a compound of formula (I), that is a prodrug which, upon administration to an animal or human being, is converted in the body to a compound of formula (I). In the case of the compounds of formula (I), such biolabile ester prodrugs are particularly advantageous in providing compounds of formula (I) suitable for oral administration. The suitability of any particular ester-forming group can be assessed by conventional in vivo animal or in vitro enzyme hydrolysis studies. Thus desirably, for optimum effect, the ester should only be hydrolysed after absorption is complete. Accordingly, the ester should be resistant to premature hydrolysis by digestive enzymes before absorption, but should be productively hydrolysed by, for example, gut-wall, plasma or liver enzymes. In this way, the active acid is released into the bloodstream following oral absorption of the prodrug.

Suitable biolabile esters may include alkyl, alkanoyloxyalkyl, cycloalkanoyloxyalkyl aroyloxyalkyl and alkoxycarbonyloxyalkyl esters, including cycloalkyl and aryl substituted derivatives thereof, aryl esters and cycloalkyl esters, wherein said alkyl, alkanoyl or alkoxy groups may contain from 1 to 8 carbon atoms and be branched-chain or straight-chain, said cycloalkyl groups may contain from 3–7 carbon atoms and said cycloalkyl groups may contain from 3–7 carbon atoms wherein both are optionally benzo-fused, and said aryl and aroyl groups include substituted phenyl, naphthyl or indanyl ring systems. Preferably, the biolabile esters of the invention are $C_1$–$C_4$ alkyl esters. More preferably, they are methyl, ethyl and t-butyl esters.

The pharmaceutically acceptable salts of the compounds of formula (I) are those formed with bases which provide non-toxic salts. Examples include the alkali and alkaline earth metal salts such as the sodium potassium or calcium salts, and salts with amines such as diethylamine.

A preferred group of compounds of formula (I) is that where $R^1$ is optionally substituted phenyl or pyridyl, $R^2$ is H, $R^3$ is $SO_2R^4$ where $R^4$ is optionally substituted phenyl, X is $CH_2$, m is 2, n is 0 or 2, and $(CH_2)_n NHR^3$ is attached at the 5-position.

Another preferred group of compounds of formula (I) is that where $R^1$ is pyridyl, $R^2$ is H, $R^3$ is $SO_2R^4$ where $R^4$ is optionally substituted phenyl or, $R^3$ is $COR^4$ where $R^4$ is alkyl, X is $CH_2$, m is 2, n is 2 and $(CH_2)_n NHR^3$ is attached at the 4-position.

Particularly preferred are such compounds wherein $R^1$ is 4-fluorophenyl, $R^2$ is H, $R^3$ is 4-arylsulphonyl, X is $CH_2$, m is 2, n is 0 and $(CH_2)_n NHR^3$ is attached at the 5-position, or wherein $R^1$ is pyridyl, $R^2$ is H, $R^3$ is 3-methylbutanoyl, X is $CH_2$, m is 2, n is 2 and $(CH_2)_n NHR^3$ is attached at the 4-position.

DETAILED DESCRIPTION OF THE INVENTION

In another aspect the present invention provides processes for the preparation of compounds of formula (I), their biolabile esters and pharmaceutically acceptable salts.

In one process, the compounds of formula (I) are obtained by hydrolysis of their lower alkyl ester precursors of formula (II):

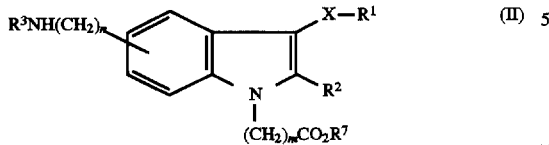

wherein $R^1$, $R^2$, $R^3$, m, n, p and X are as defined for formula (I) and $R^7$ is $C_1-C_4$ alkyl, preferably methyl, ethyl or t-butyl. The reaction can be conducted under basic or acidic conditions, e.g. with excess aqueous alkali, preferably sodium hydroxide solution, or excess hydrochloric acid respectively, optionally with a suitable co-solvent such as a $C_1-C_4$ alkanol, preferably methanol, at from ambient temperature to the reflux temperature of the reaction medium.

In the case where $R^1$=H and X=$CH_2$ (i.e. a 3-methylindole), the final compounds may be prepared by hydrogenolysis of the compound where $R^1$=1-imidazolyl and X=$CH_2$.

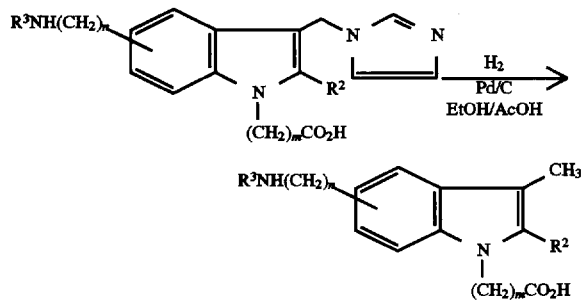

The compounds of formula (II) where $R^3$ is $SO_2R^4$ or $COR^4$ may generally be prepared by sulphonation/sulphamoylation or acylation, respectively of an amine of formula (III):

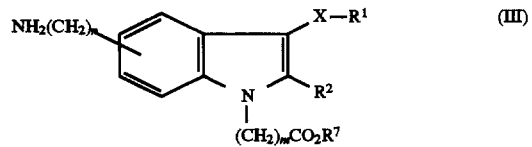

where $R^1$, $R^2$, $R^7$, m, n and X are as defined above. Sulphonylation may be carried out by reaction of the amine of formula (III) with a sulphonyl halide of formula $R^4SO_2Hal$, where Hal is a halogen atom (preferably the chloride), or with a sulphonic anhydride of formula $(R^4SO_2)_2O$, where $R^4$ is as defined above but is other than $NR^5R^6$. Sulphamoylation may be carried out similarly by reaction of compound (III) with a sulphamoyl halide (preferably the chloride) of formula $R^5R^6NSO_2Hal$, to yield a compound of formula (II) in which $R^4$ is $NR^5R^6$.

Acylation may be carried out by reaction of compound (III) with an acid anhydride of formula $(R^4CO)_2O$ or acid halide $R^4CO$ Hal (preferably the chloride) where $R^4$ is as defined above.

These reactions may be carried out in the presence of a base such as triethylamine, pyridine, 4-dimethylaminopyridine or combination thereof to act as an acid scavenger in a suitable solvent such as methylene chloride or tetrahydrofuran.

Alternatively, the acylation may be carried out by reaction of compound (III) with an imidazolide of formula

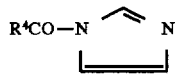

generated in situ by reaction of an acid of formula $R^4CO_2H$ and carbonyldiimidazole in a solvent such as tetrahydrofuran, dimethylformamide or methylene chloride.

The novel compounds of formula (II) and (III) above are themselves part of the present invention.

The amines of formula (III) may be prepared by different methods, depending on the value of n. When n=2 the amine may be prepared by amine deprotection from a corresponding carbamate of formula (IV):

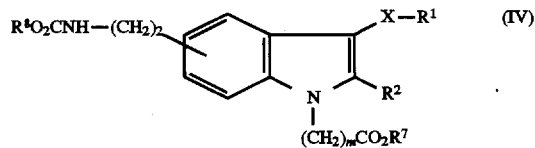

where $R^1$, $R^2$, $R^7$, m and X are as defined above and $R^8$ is a group which can be selectively removed in the presence of group $R^7$ to give the required amine. A suitable $R^8$ group is benzyl, which may be removed by catalytic transfer hydrogenation using ammonium formate and a palladium/carbon catalyst in a suitable solvent such as a methanol/tetrahydrofuran mixture at reflux temperature. Alternatively, this benzyl group may be removed by hydrogenation using hydrogen, at a pressure of 1–5 atmospheres, in the presence of a palladium/carbon catalyst and a solvent such as tetrahydrofuran, methanol or ethanol at a temperature from ambient to 50° C. Another possible $R^8$ is t-butyl, which may be removed by reaction with an acid such as hydrochloric or trifluoroacetic acid in a solvent such as dichloromethane at a temperature from 0° to 20° C.

When n=1 the amine of formula (III) may be prepared by reduction of a nitrile of formula (V):

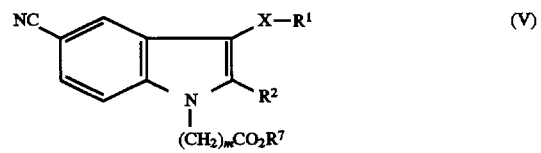

where $R^1$, $R^2$, $R^7$, X and m are as defined above. This reduction may be performed by hydrogenation in the presence of a metal catalyst such as rhodium/alumina, preferably in the presence of ammonia, or Raney nickel under the usual conditions for this reaction. Reduction may also be carried out by means of diborane.

When n=0 the desired amines of formula (III) may be prepared by reduction of corresponding nitro compounds of formula (VI):

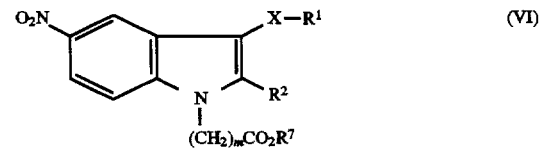

where $R^1$, $R^2$, $R^7$, m and X are as defined above. This reduction may be achieved by treatment with hydrogen, typically at a pressure of 1–5 atmospheres, in a suitable solvent such as methanol or ethanol with a catalyst such as palladium/carbon at a temperature of up to 50° C.

The carbamates of formula (IV) may be prepared from carboxylic acids of formula (VII):

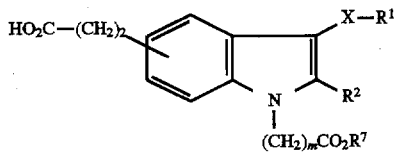 (VII)

where $R^1$, $R^2$, $R^7$, X and m are as defined above by reaction with diphenylphosphoryl azide in a suitable solvent, such as dioxan, at reflux in the presence of $Et_3N$ to form an acyl azide which undergoes the Curtius re-arrangement to give the corresponding isocyanate. Addition of an alcohol, such as benzyl or t-butyl alcohol, gives the corresponding carbamate (IV). Excess alcohol may be used as the solvent in place of dioxan.

The acids of formula (VII) may themselves be prepared from acrylic esters of formula (VIII):

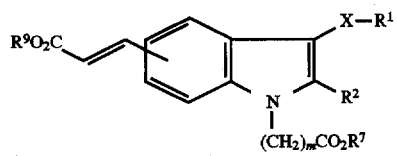 (VIII)

where $R^1$, $R^2$, $R^7$, m and X are as defined above and $R^8$ is a group such as benzyl or t-butyl. Catalytic transfer hydrogenation or conventional hydrogenation, as described above in relation to compounds (IV), reduces the double bond of the acrylic substituent and, when $R^9$ is benzyl, also removes the $R^9$ group to yield an acid of formula (VII). When $R^9$ is a group not removed by hydrogenolysis, such as t-butyl, it may be removed by treatment with a strong acid, such as hydrochloric or trifluoroacetic acid, before or after hydrogenation of the acrylic double bond.

The esters of formula (VIII), nitriles of formula (V) and nitro compounds of formula (VI) may all be prepared from indole compounds of formula (IX):

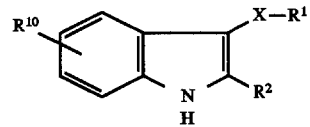 (IX)

where $R^1$, $R^2$ and X are as defined above and $R^{10}$ is

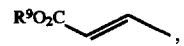,

CN or $NO_2$, respectively. When m=2 compound (IX) may be allowed to react with compound

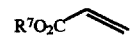

in the presence of a base catalyst to give compound (VIII), (V) or (VI) by Michael addition. When m=3 these compounds may be obtained by reaction of compound (IX) with an ester of formula Hal-$(CH_2)_3$—$CO_2R^7$, where Hal is chloro, bromo or iodo, in the presence of a base such as sodium hydride in dimethylformamide as a solvent.

When $R^{10}$ is the acrylic ester group

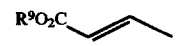

compound (IX) may be obtained from a bromoindole of formula (X):

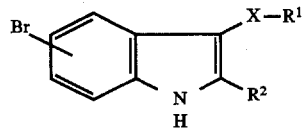 (X)

where $R^1$, $R^2$ and X are as defined above by a Heck reaction with an appropriate acrylic ester in the presence of palladium (II) acetate, tri-o-tolylphosphine and a base such as triethylamine in a suitable solvent such as acetonitrile or dimethylformamide at a temperature from 80° to 160° C.

When $R^{10}$ is CN compound (IX) may be prepared from compound (X) by reaction of the latter with a cyanide, such as CuCN in a solvent such as dimethylformamide, dimethylacetamide or N-methylpyrrolidone at reflux temperature.

When indole intermediates in which X is $CH_2$, $R^2$ is $C_1$–$C_4$ alkyl and $R^1$ is not 1-imidazolyl are to be obtained, compounds (IX or X) in which X is a direct link and $R^1$ is H, $R^2$ is $C_1$–$C_4$ alkyl may be obtained by the above-described methods and subsequently allowed to react with an appropriate aldehyde in the presence of trifluoroacetic acid and triethylsilane:

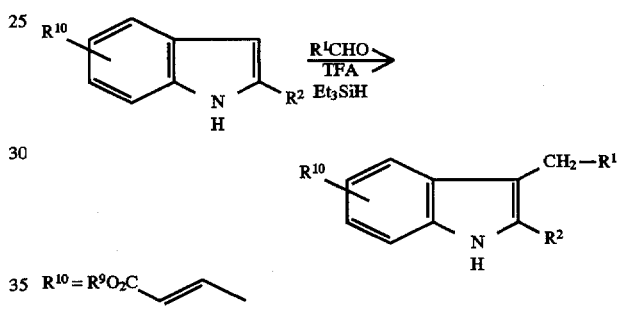

When X is $CH_2$ and $R^1$ is a 1-imidazolyl group in the desired compound the following synthesis may be used:

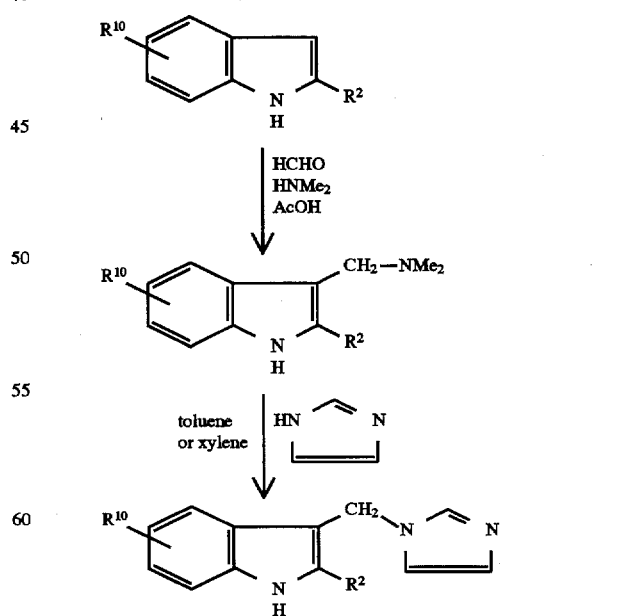

In this synthesis the starting compound in which $R^2$ is as defined above and $R^{10}$ is

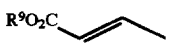

or CN reacts with formaldehyde, dimethylamine and acetic acid to give the corresponding indole having a —CH$_2$NMe$_2$ substituent at the 3-position. Subsequent treatment with imidazole in a solvent such as toluene or xylene, at the boiling point of the solvent, results in replacement of the —NMe$_2$ group with a 1-imidazolyl group.

The bromo-indole intermediates of formula (X) may be prepared from known compounds by standard methods, such as the Fischer indole synthesis or by substitution of bromocompounds (X) in which X is a direct link and R$^1$ is H. For example, a compound of formula (XI):

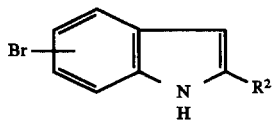

(XI)

where R$^2$ is as defined above may be converted to a compound (X) where X is CH$_2$ by reaction with aldehyde R$^1$CHO in the presence of trifluoroacetic acid and Et$_3$SiH, or with a Grignard reagent MeMgHal where Hal is a halogen atom followed by reaction with halide R$^1$CH$_2$Cl or R$^1$CH$_2$Br.

The nitroindole intermediates (IX) in which R$^{10}$ is NO$_2$ may be made by known methods, such as the Fischer indole synthesis applied to the appropriate nitrophenylhydrazone. When X is CH$_2$ and R$^1$ is imidazolyl these intermediates may be prepared from those in which X is a direct link and R$^1$ is H by reaction with formaldehyde/dimethylamine/acetic acid followed by reaction with imidazole, as described above.

As previously mentioned, the compounds of the invention are able to antagonise the action of thromboxane A$_2$ and prostaglandin H$_2$ at the thromboxane A$_2$ receptor.

Thromboxane A$_2$ (TXA$_2$) is a naturally occurring prostanoid which is known to be a potent vasoconstrictor and platelet aggregating agent. TXA$_2$ is also believed to be involved in a number of disease states including atherosclerosis, ischaemic heart disease, peripheral vascular disease and myocardial infarction. TXA$_2$ acts at the thromboxane A$_2$ receptor, at which site other prostanoids, notably prostaglandin H$_2$, may also be agonists.

TXA$_2$ synthetase inhibitors prevent formation of TXA$_2$ from the precursor PGH$_2$ which may be diverted to produce more of the vasodilator and antiaggregatory PGI$_2$. However, a possible drawback with this type of agent is that accumulated PGH$_2$ substrate can activate the TXA$_2$ receptor, thus partly eliminating or negating the benefit of suppressing TXA$_2$ formation. Furthermore, if inhibition of TXA$_2$ synthetase is incomplete, sufficient TXA$_2$ may be available to induce some platelet activation. Both of these drawbacks can be overcome if a TXA$_2$ receptor antagonist is present to block the action of any TXA$_2$ or accumulated PGH$_2$ substrate. It has been demonstrated that combination of a TXA$_2$ antagonist and a TXA$_2$ synthetase inhibitor produces a synergistic effect on platelet aggregation in vitro (Watts et al., Brit. J. Pharmacol., 102, 497, 1991). In addition, administration of the TXA$_2$ antagonist sulotroban and the TXA$_2$ synthetase inhibitor dazoxiben to human volunteers gave a stronger inhibition of platelet aggregation than either agent alone (Gresele et al.,). Clin. Invest., 80, 1435, 1987).

Thus the compounds of the invention are of particular value when used in combination with a selective inhibitor of the thromboxane synthetase enzyme and the resulting combinations will find utility in the disease states already mentioned as well as those in which PGD$_2$ and PGF$_{2\alpha}$ may be implicated as mediators, such as diabetes, bronchial asthma, and other inflammatory conditions.

Thus the present invention also provides a pharmaceutical composition comprising as active ingredients a novel TXA$_2$ receptor antagonist of the formula (I) as hereinbefore defined and a TXA$_2$ synthetase inhibitor, together with a pharmaceutically acceptable diluent or carrier.

Suitable TXA$_2$ synthetase inhibitors for inclusion as active ingredients in the composition according to the invention include, for example, the known compounds:

1) 4-[2-(1H-imidazol-1-yl)ethoxy]benzoic acid, (dazoxiben, R. P. Dickinson, et al, J. Med. Chem., 1985, 28, 1427–1432);
2) 3-(1H-imidazol-1-ylmethyl)-2-methyl-1H-indole-1-propanoic acid, (dazmegrel, R. P. Dickinson, et al, J. Med. Chem., 1986, 29, 342–346);
3) 2-methyl-3-(3-pyridylmethyl)-1H-indole-1-propanoic acid, (European patent 0054417);
4) 3-methyl-2-(3-pyridylmethyl)benzo[b]thiophene-5-carboxylic acid, (UK-49,883, P. E. Cross, R. P. Dickinson, Spec Publ. Royal Soc. Chem. No. 50, p. 268–285, 1984);
5) 1,3-dimethyl-2-(1H-imidazol-1-ylmethyl)-1H-indol-5-carboxylic acid, (R. P. Dickinson et al, J. Med. Chem., 1986, 29, 1643–1650);
6) a carboxy, lower alkoxycarbonyl or carbamoyl substituted benzothiophene, benzofuran or indole as claimed in European patent 0073663, or the novel compound:
7) 2-methyl-3-(3-pyridyl)-1H-indole-1-pentanoic acid; or any other thromboxane synthetase inhibitor which acts in a synergistic manner and is chemically compatible with the novel compounds of formula (I).

Many of the compounds of the invention also inhibit the thromboxane synthetase enzyme in addition to their action as thromboxane receptor antagonists. Such compounds may therefore be effective in the absence of an additional thromboxane synthetase inhibitor. The biological activity of the compounds of the invention can be demonstrated using the following in vitro and in vivo assay procedures.

1. Thromboxane A$_2$ receptor antagonism

Spirally cut rat aortic strips, mounted for isometric tension recording in 20 ml organ baths, are bathed in Krebs-bicarbonate solution at 37° C. Following an incubation period of 2 hours under 1 gram resting tension, the tissues are pre-treated with U-46619 (a thromboxane A2 receptor agonist) for 10 minutes, then washed and the tissues allowed to equilibriate for a further 1 hour. Cumulative doses of U-46619 over the range 1 nM–100 nM are sequentially included in the bathing fluid and increases in the tissue tension noted.

The test compounds are incubated with the tissue for 15 minutes prior to repeating the cumulative dosing of U-46619 and the ability of the compound to antagonize the thromboxane A$_2$ receptor is determined from the dose-response curves for U-46619 in the presence of varied concentrations of the test compound.

2. Anaesthetised Rabbits

Thromboxane A$_2$ receptor antagonism is evaluated ex vivo in anaesthetised rabbits as follows:

New Zealand White rabbits (2–2.5 kg) are anaesthetised with fentanyl citrate (0.1 89 mg) and fluanisone (6 mg) intramuscularly and midazolam (3 mg) intravenously and maintained by an intravenous infusion of fentanyl citrate (0.315 mg), fluanisone (1 mg) and midazolam (1 mg) per hour. After cannulation of the trachea, a carotid artery is cannulated for collection of blood samples. The catheter is kept patent by the presence within the catheter of saline containing heparin (50 μ/ml). Control carotid arterial blood samples are taken 25 and 5 minutes prior to administration of the test compound via a marginal ear vein. Two groups of rabbits are used. The first group receives 0.01 mg/kg of the test compound followed, at ten minute intervals, by 0.03, 0.1, 0.3, 1.0, 3.0 and 10 mg/kg doses; the second group comprises the controls. Carotid arterial blood samples are taken 5 minutes after all doses. At each time point, a 900 μl blood sample is immediately mixed with 100 μl of trisodium citrate (3.15%). After 90 minutes incubation at room temperature, this sample is mixed in equal proportions with an aggregometry buffer (J. Pharmacol. Methods, 1981, 6, 315) and brought to 37° C. Electrodes for the measurement of electrical impedance are placed in the blood and U-46619 (final concentration 3 μM) is added to the blood. Antagonism of platelet thromboxane $A_2$ receptors by the compound is assessed by comparing the change in electrical impedance produced by U-46619 in compound-treated rabbits with the untreated controls.

3. Conscious Dogs

Thromboxane $A_2$ receptor antagonism may also be evaluated ex vivo in sling-restrained conscious dogs after oral (p.o.) or intravenous (i.v.) administration of a compound of the invention. The sampling and assaying procedures employed are similar to those described for the ex vivo anaesthetised rabbit experiments.

For administration to man, in the therapy or prevention of diseases or adverse medical conditions in which $TXA_2$ is implicated as a causative agent, oral dosages of the compounds would be expected to be in the range of from 20–800 mg daily for an average adult patient (70 kg). Thus for a typical adult patient, individual tablets or capsules contain from 10 to 400 mg of active compound, in a suitable pharmaceutically acceptable vehicle or carrier, for administration as a single dose, or in multiple doses, once or several times a day. Dosages for intravenous administration would typically be within the range of from 5 to 400 mg per single dose required. In practice the physician will determine the actual dosage which will be most suitable for an individual patient and it will vary with the age, weight and response of the particular patient, and with the condition being treated. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example enough salts or glucose, to make the solution isotonic with blood.

Thus the invention provides a pharmaceutical composition comprising a compound of formula (I), or a pharmaceutically acceptable salt or biolabile ester thereof, together with a pharmaceutically acceptable diluent or carrier.

The invention also provides a compound of formula (I), or a pharmaceutically acceptable salt or biolabile ester thereof, or a pharmaceutical composition containing any of these entities, for use in medicine.

The invention further includes the use of a compound of formula (I), or a pharmaceutically acceptable salt or a biolabile ester thereof, for the manufacture of a medicament for the treatment of disease conditions in which thromboxane $A_2$ is a causative agent.

In a further aspect, the invention provides a method of treating or preventing disease conditions in which thromboxane $A_2$ is a causative agent in a mammal (including a human being) which comprises administering to said mammal a therapeutically effective amount of a compound of formula (I), or a pharmaceutically acceptable salt, or a biolabile ester thereof.

The invention also includes any novel intermediates disclosed herein.

The synthesis of the compounds of the invention and of the intermediates for use in their preparation are illustrated by the following Examples and Preparations. The purity of the compounds was routinely monitored by thin layer chromatography (TLC) using Merck Kieselgel 60 $F_{254}$ plates and the following solvent systems (SS):

1. Dichloromethane;
2. Dichloromethane:methanol, 95:5;
3. Dichloromethane:methanol:0.880 ammonia, 90:10:1;
4. Toluene:diethylamine, 9:1;
5. Dichloromethane:methanol:0.880 ammonia, 100:20:1;
6. Dichloromethane:ethanol:ammonia, 98:2:0.2;
7. Dichloromethane:ethanol:ammonia, 90:10:1;

$^1$H-Nuclear magnetic reasonance (NMR) spectra were recorded using either a Nicolet QE-300 or a Bruker AC-300 spectrometer and were in all cases consistent with the proposed structures. Chemical shifts are given in parts-per-million downfield from tetramethylsilane using conventional abbreviations for designation of major peaks: s, singlet; d, doublet; t, triplet; m, multiplet and br, broad.

EXAMPLE 1

Methyl 5-[2-[[(4-fluorophenyl)sulphonyl]amino]ethyl]-3-(3-pyridylmethyl)-1H-indole-1-propanoate 4-Fluorobenzenesulphonyl chloride (0.346 g) was added portionwise to a stirred solution of methyl 5-(2-aminoethyl)-3-(3-pyridylmethyl)-1H-indole1-propanoate (0.50 g) and triethylamine (0.33 g) in dichloromethane (5 ml) at room temperature. The mixture was stirred for 30 minutes and then washed with water and dried (MgSO$_4$). The solvent was evaporated and the residue was chromatographed on silica gel using dichloromethane/methanol (50:1) as eluant. The product fractions were combined and evaporated to give the title compound as a gum (0.59 g).

Found: C,62.89; H,5.22; N,8.15. $C_{26}H_{26}FN_3O_4S$ requires: C,63.01; H,5.29; N,8.48%.

EXAMPLES 2 to 27

The compounds of the following formula were prepared as in Example 1 using the appropriate sulphonyl chloride, sulphamoyl chloride or acyl chloride and the appropriate indole compound.

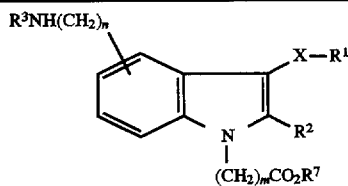

| Ex | $R^1$ | $R^2$ | $R^3NH-(CH_2)_n$ position | $R^3$ | $R^7$ | n | m | x | Solvent, Base | m.p. °C. | Analytical Data |
|---|---|---|---|---|---|---|---|---|---|---|---|
| 2 | 1-imidazolyl | H | 5 | 4-fluoro-phenyl sulphonyl | Me | 0 | 2 | $CH_2$ | $CH_2Cl_2$, $Et_3N$ | Foam | Found: C, 57.93; H, 4.66; N, 12.13; $C_{22}H_{21}FN_4O_4S$ requires: C, 57.88; H, 4.64; N, 12.27%. |
| 3 | 1-imidazolyl | Me | 5 | 4-fluoro-phenyl sulphonyl | Me | 0 | 2 | $CH_2$ | $CH_2Cl_2$, Pyridine | Foam | Found: C, 58.45; H, 4.94; N, 11.56; $C_{23}H_{23}FN_4O_4S$ requires: C, 58.71; H, 4.93; N, 11.91%. |
| 4 | 4-fluorophenyl | H | 5 | 4-fluoro-phenyl sulphonyl | Me | 0 | 2 | $CH_2$ | $CH_2Cl_2$, $Et_3N$ | 115–118 | Found: C, 61.55; H, 4.24; N, 5.90. $C_{25}H_{22}F_2N_2O_4S$ requires: C, 61.97; H, 4.58; N, 5.78%. |
| 5 | 4-fluorophenyl | H | 5 | 4-chloro-phenyl sulphonyl | Me | 0 | 2 | $CH_2$ | $CH_2Cl_2$, $Et_3N$ | 120–123 | Found: C, 60.14; H, 4.35; N, 5.56; $C_{25}H_{22}ClFN_2O_4S$ requires: C, 59.94; H, 4.43; N, 5.59%. |
| 6 | 3-pyridyl | H | 5 | 4-chloro-phenyl sulphonyl | Me | 0 | 2 | direct link | $CH_2Cl_2$, $Et_3N$ | 176–178 | Found: C, 58.96; H, 4.13; N, 8.79; $C_{23}H_{20}ClN_2O_4S$ requires: C, 58.78; H, 4.29; N, 8.94%. |
| 7 | 3-pyridyl | H | 5 | 4-chloro-phenyl sulphonyl | Et | 0 | 3 | direct link | $CH_2Cl_2$, $Et_3N$ | 209–211 | Found: C, 60.11; H, 4.83; N, 8.33; $C_{25}H_{24}ClN_2O_4S$ requires: C, 60.29; H, 4.86; N, 8.44%. |
| 8 | 3-pyridyl | H | 5 | 4-fluoro-phenyl sulphonyl | Me | 0 | 2 | $CH_2$ | $CH_2Cl_2$, $Et_3N$ | Foam | Found: C, 61.66; H, 4.63; N, 8.95; $C_{24}H_{22}FN_2O_4S$ requires: C, 61.65; H, 4.74; N, 8.99%. |
| 9 | 3-pyridyl | H | 5 | 4-fluoro-phenyl sulphonyl | Me | 0 | 3 | $CH_2$ | $CH_2Cl_2$, $Et_3N$ | Foam | Found: C, 63.01; H, 5.35; N, 8.32; $C_{26}H_{26}FN_2O_4S$ requires: C, 63.01; H, 5.29; N, 8.48%. |
| 10 | 1-imidazolyl | Me | 5 | 4-fluoro-phenyl sulphonyl | Me | 2 | 2 | $CH_2$ | $CH_2Cl_2$, Pyridine | Foam | Rf. 0.55(SS3) δ($CDCl_3$): 2.47(3H, s), 2.74–2.87(4H, m), 3.24(2H, m), 3.69(3H, s), 4.43(2H, t), 4.62(1H, t), 5.20(2H, s), 6.86(1H, s), 6.92(1H, dd), 7.02(1H, s), 7.05–7.15 (3H, m), 7.23(1H, d), 7.49(1H, s), 7.77(2H, m). |
| 11 | 1-imidazolyl | Me | 4 | 4-fluoro-phenyl sulphonyl | Me | 2 | 2 | $CH_2$ | $CH_2Cl_2$, DMAP | Foam | Found: C, 59.98; H, 5.53; N, 10.94; $C_{26}H_{27}FN_4O_4S$ requires: C, 60.22; H, 5.46; N, 11.24%. |
| 12 | 3-pyridyl | H | 5 | methyl-sulphonyl | Me | 2 | 2 | $CH_2$ | $CH_2Cl_2$, $Et_3N$ | Gum | Found: C, 59.37; H, 5.89; N, 9.71; $C_{21}H_{25}N_3O_4S$. $0.1CH_2Cl_2$ requires: C, 59.77; H, 5.99; N, 9.91%. |
| 13 | 3-pyridyl | H | 5 | dimethyl-amino-sulphonyl | Me | 2 | 2 | $CH_2$ | $CH_2Cl_2$, DMAP/ $Et_3N$ (1.5:1) | Gum | Rf. 0.6(SS3) δ($CDCl_3$): 2.75(6H, s), 2.82(2H, t), 2.94(2H, t), 3.34(2H, m), 3.67(3H, s), 4.08(2H, s), 4.14(1H, t), 4.42(2H, t), 6.87(1H, s), 7.08(1H, d), 7.20–7.24(1H, m), 7.29–7.32 (2H, m), 7.55(1H, d), 8.46(1H, d), 8.60(1H, s). |
| 14 | 3-pyridyl | H | 5 | 3-methyl-butanoyl | Me | 2 | 2 | $CH_2$ | $CH_2Cl_2$, $Et_3N$ | Gum | Found: C, 68.52; H, 7.09; N, 9.59; $C_{25}H_{31}N_3O_3$. $0.25CH_2Cl_2$ requires: C, 68.49; H, 7.17; |

-continued

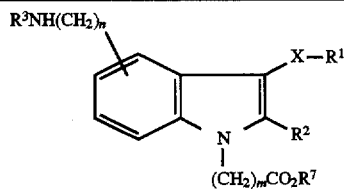

| Ex | R¹ | R² | R³NH—(CH₂)ₙ position | R³ | R⁷ | n | m | x | Solvent, Base | m.p. °C. | Analytical Data |
|---|---|---|---|---|---|---|---|---|---|---|---|
| 15 | 3-pyridyl | H | 4 | 4-fluoro-sulphonyl | Me | 2 | 2 | CH₂ | CH₂Cl₂, Et₃N | Gum | N, 9.49%. Rf. 0.6(SS3) δ(CDCl₃): 2.78(2H, t), 3.00(2H, t), 3.13(2H, m), 3.65(3H, s), 4.13(2H, s), 4.35–4.44(3H, m), 6.72 (1H, s), 6.74(1H, d), 7.07–7.24(5H, m), 7.41(1H, d), 7.74(1H, m), 8.44(2H, m). |
| 16 | 3-pyridyl | H | 4 | dimethyl-amino sulphonyl | Me | 2 | 2 | CH₂ | CH₂Cl₂, Et₃N | Gum | Rf. 0.5(SS3) δ(CDCl₃): 2.70(6H, s), 2.79(2H, m), 3.08(2H, t), 3.26(2H, m), 3.66(3H, s), 4.10(1H, t), 4.23(2H, s), 4.38(2H, t), 6.74(1H, s), 6.88(1H, d), 7.13–7.23 (3H, m), 7.46(1H, d), 8.46–8.49(2H, m). |
| 17 | 3-pyridyl | H | 4 | 3-methyl butanoyl | Me | 2 | 2 | CH₂ | CH₂Cl₂, Et₃N/DMAP(1:1) | 113–115 | Found: C, 71.61; H, 7.11; N, 9.96; C₂₅H₃₁N₃O₃ requires: C, 71.23; H, 7.41; N, 9.97%. |
| 18 | 3-pyridyl | Me | 5 | 4-fluoro-phenyl sulphonyl | Me | 2 | 2 | CH₂ | CH₂Cl₂, Et₃N | Gum | Rf. 0.55(SS2) δ(CDCl₃): 2.39(3H, s), 2.71–2.80(4H, m), 3.17–3.24(2H, m), 3.67(3H, s), 4.01(2H, s), 4.34–4.43 (3H, m), 6.85(1H, d), 7.02 (1H, s), 7.05–7.15(3H, m), 7.20(1H, d), 7.39(1H, d), 7.70–7.75(2H, m), 8.40(1H, d), 8.49(1H, s). |
| 19 | 3-pyridyl | Me | 5 | 4-iodo-phenyl-sulphonyl | Me | 2 | 2 | CH₂ | CH₂Cl₂, Et₃N | Foam | Found: C, 52.89; H, 4.55; N, 6.75; C₂₇H₂₈IN₂O₄S requires: C, 52.51; H, 4.57; N, 6.81%. |
| 20 | 3-pyridyl | Me | 5 | 4-trifluoro-methyl phenyl sulphonyl | Me | 2 | 2 | CH₂ | CH₂Cl₂, Et₃N | Foam | Found: C, 59.99; H, 5.09; N, 7.34; C₂₈H₂₈F₃N₂O₄S requires: C, 60.09; H, 5.04; N, 7.51%. |
| 21 | 3-pyridyl | Me | 4 | 4-fluoro-phenyl sulphonyl | Me | 2 | 2 | CH₂ | CH₂Cl₂, Et₃N | Gum | Rf. 0.7(SS3) δ(CDCl₃): 2.35(3H, s), 2.76(2H, t), 2.89(2H, t), 3.05(2H, m), 3.68(3H, s), 4.14(2H, s), 4.39–4.48 (3H, m), 6.70(1H, d), 7.05–7.12(4H, m), 7.20–7.26(2H, m), 7.68–7.72(2H, m), 8.33–8.38 (2H, m). |
| 22 | H | H | 5 | 4-chloro-phenyl sulphonyl | Me | 0 | 2 | direct link | CH₂Cl₂, Et₃N | Gum | Found: C, 55.21; H, 4.36; N, 6.74; C₁₈H₁₇ClN₂O₄S requires: C, 55.04; H, 4.36; N, 7.13%. |
| 23 | H | H | 5 | 4-fluoro-phenyl sulphonyl | Me | 0 | 2 | direct link | CH₂Cl₂, Et₃N | Gum | Found: C, 57.41; H, 4.61; N, 7.32; C₁₈H₁₇FN₂O₄S requires: C, 57.44; H, 4.55; N, 7.44%. |
| 24 | 4-fluoro-phenyl | H | 5 | Phenyl-sulphonyl | Me | 0 | 2 | CH₂ | CH₂Cl₂, Et₃N | 109–112 | Found: C, 64.65; H, 5.05; N, 5.91; C₂₅H₂₃FN₂O₄S requires: C, 64.36; H, 4.97; N, 6.00%. |
| 25 | 4-fluoro-phenyl | H | 5 | 4-trifluoro-methyl- | Me | 0 | 2 | CH₂ | CH₂Cl₂, Et₃N | 100–103 | Found: C, 58.30; H, 4.09; N, 5.38; |

-continued

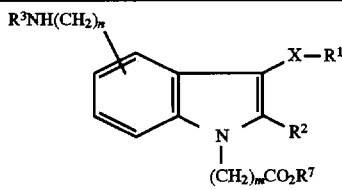

| Ex | R¹ | R² | R³NH—(CH₂)ₙ position | R³ | R⁷ | n | m | x | Solvent, Base | m.p. °C. | Analytical Data |
|---|---|---|---|---|---|---|---|---|---|---|---|
| 26 | 4-fluoro-phenyl | H | 5 | phenyl-sulphonyl 4-methoxy-phenyl-sulphonyl | Me | 0 | 2 | CH₂ | CH₂Cl₂, Et₃N | 161–162 | $C_{26}H_{22}F_4N_2O_4S$ requires: C, 58.42; H, 4.15; N, 5.24%. Found: C, 62.91; H, 5.00; N, 5.43; $C_{26}H_{25}FN_2O_5S$ requires: C, 62.89; H, 5.07; N, 5.64%. |
| 27 | 4-fluoro-phenyl | H | 5 | 4-methyl-phenyl-sulphonyl | Me | 0 | 2 | CH₂ | CH₂Cl₂, Et₃N | 145–148 | Found: C, 65.06; H, 5.32; N, 5.85; $C_{26}H_{25}FN_2O_4S$ requires: C, 64.98; H, 5.24; N, 5.83%. |

EXAMPLE 28

Methyl 5-[[(2-cyclopropyl)acetyl]amino]ethyl-3-(3-pyridylmethyl))-1H-indole-1-propanoate A mixture of cyclopropylacetic acid (0.25 g) and carbonyldiimidazole (0.288 g) in dry tetrahydrofuran (9 ml) was heated under reflux until evolution of $CO_2$ ceased. A solution of methyl 5-(2-aminoethyl)-3-(3-pyridylmethyl)-1H-indole-1-propanoate (0.50 g) in dry dichloromethane (5 ml) was added and the solution was stirred at room temperature for 56 hours and then evaporated. The residue was partitioned between ethyl acetate and water. The organic layer was washed twice with water, dried (MgSO₄) and evaporated. The residue was chromatographed on silica gel. Elution with dichloromethane gave starting material, and then further elution with dichloromethane/methanol (19:1) gave pure product. The product fractions were evaporated to give the title compound as a gum (0.497 g). Rf. 0.7 (SS3).

$\delta(CDCl_3)$: 0.10(2H,m), 0.48(2H,m), 0.85(1H,m), 2.10 (2H,d), 2.82(2H,t) 2.91(2H,t), 3.57(2H,m), 3.67(3H,s), 4.07 (2H,s), 4.42(2H,t), 5.90(1H,br), 6.85(1H,s), 7.08(1H,d), 7.22(1H,m), 7.29–7.32(2H,m), 7.57(1H,d), 8.48(1H,d), 8.57 (1H,s).

EXAMPLE 29

5-[(4-Fluorophenyl)sulphonyl]amino-3-(3-pyridylmethyl)-1H-indole-1-propanoic acid A mixture of methyl 5-[(4-fluorophenyl)sulphonyl]-amino-3-(3-pyridylmethyl)-1H-indole-1-propanoate (the product of Example 8) ((1.10 g), sodium hydroxide (0.47 g), methanol (2 ml) and water (10 ml) was heated under reflux for 75 minutes and then evaporated to a small volume. The solution was acidified with acetic acid to give a gum which solidified on scratching. The solid was filtered off, washed with water and dried. Crystallisation from ethyl acetate/methanol gave the title compound (0.64 g), m.p. 214°–215° C. Found: C,61.18; H,4.23; N,9.28. $C_{23}H_{20}FN_3O_4S$ requires: C,60.91; H,4.44; N,9.26%.

EXAMPLES 30–56

The procedure of Example 29 was repeated but using the appropriate starting material to produce compounds of the following formula given in the following Table:

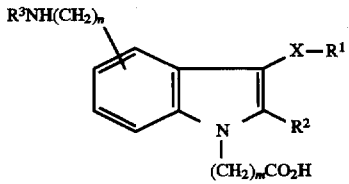

| Ex | R¹ | R² | R³NH(CH₂)ₙ position | R³ | n | m | x | m.p. °C. | Analytical Data |
|---|---|---|---|---|---|---|---|---|---|
| 30 | 1-imidazolyl | H | 5 | 4-fluorophenyl sulphonyl | 0 | 2 | CH₂ | 208–210 | Found: C, 57.47; H, 4.15; N, 12.60; $C_{21}H_{19}FN_4O_4S$ requires: C, 57.00; H, 4.33; N, 12.66%. |
| 31 | 1-imidazolyl | Me | 5 | 4-fluorophenyl sulphonyl | 0 | 2 | CH₂ | Foam | Rf. 0.1(SS3) $\delta(CDCl_3)$: 2.44(3H, s), 2.60(2H, t), 4.27(2H, t), 5.19(2H, s), 6.77(1H, d), 6.82(1H, s), 6.89(1H, s), 7.18(1H, s), 7.29–7.33(3H, m), 7.58(1H, s), 7.66–7.70(2H, m), 9.97(1H, s). |

-continued

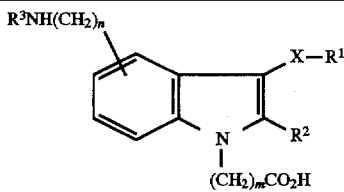

| Ex | R¹ | R² | R³NH(CH₂)ₙ position | R³ | n | m | x | m.p. °C. | Analytical Data |
|---|---|---|---|---|---|---|---|---|---|
| 32 | 4-fluorophenyl | H | 5 | 4-fluorophenyl sulphonyl | 0 | 2 | CH₂ | 185–188 | Found: C, 60.78; H, 4.19; N, 5.74; $C_{24}H_{20}F_2N_2O_4S$ requires: C, 61.27; H, 4.28; N, 5.75%. |
| 33 | 4-fluorophenyl | H | 5 | 4-chlorophenyl sulphonyl | 0 | 2 | CH₂ | 144–147 | Found: C, 59.33; H, 3.93; N, 5.55; $C_{24}H_{20}ClFN_2O_4S$ requires: C, 59.20; H, 4.14; N, 5.75%. |
| 34 | 3-pyridyl | H | 5 | 4-chlorophenyl sulphonyl | 0 | 2 | direct link | 235–237 | Found: C, 58.28; H, 3.71; N, 9.04; $C_{22}H_{18}ClN_3O_4S$ requires: C, 57.95; H, 3.98; N, 9.22%. |
| 35 | 3-pyridyl | H | 5 | 4-chlorophenyl sulphonyl | 0 | 3 | direct link | 199–201 | Found: C, 58.63; H, 4.16; N, 8.81; $C_{23}H_{20}ClN_3O_4S$ requires: C, 58.78; H, 4.29; N, 8.94%. |
| 36 | 3-pyridyl | H | 5 | 4-fluorophenyl sulphonyl | 0 | 3 | CH₂ | 154–156 | Found: C, 61.80; H, 4.68; N, 8.91; $C_{24}H_{22}FN_3O_4S$ requires: C, 61.65; H, 4.74; N, 8.99%. |
| 37 | 1-imidazolyl | Me | 5 | 4-fluorophenyl sulphonyl | 2 | 2 | CH₂ | 165–167 | Found: C, 58.99; H, 5.40; N, 10.96; $C_{24}H_{25}FN_4O_4S$ requires: C, 59.49; H, 5.70; N, 11.57%. |
| 38 | 1-imidazolyl | Me | 4 | 4-fluorophenyl-sulphonyl | 2 | 2 | CH₂ | Foam | Rf. 0.15(SS3). δ(DMSOd₆): 2.45(3H, s), 2.63(2H, t), 2.79(2H, t), 2.85(2H, m), 4.37(2H, t), 5.24(2H, s), 6.72(1H, d), 6.82(1H, s), 6.88(1H, s), 6.98(1H, dd), 7.30–7.40 (3H, m), 7.45(1H, s), 7.79(2H, m), 8.91 (1H, t). |
| 39 | 3-pyridyl | H | 5 | 4-fluorophenyl-sulphonyl | 2 | 2 | CH₂ | 158–160 | Found: C, 61.98; H, 5.26; N, 8.52; $C_{25}H_{24}FN_3O_4S$ requires: C, 62.35; H, 5.02; N, 8.73%. |
| 40 | 3-pyridyl | H | 5 | methylsulphonyl | 2 | 2 | CH₂ | 180–182.5 | Found: C, 60.07; H, 5.78; N, 10.25; $C_{20}H_{23}N_3O_4S$ requires: C, 59.83; H, 5.77; N, 10.47%. |
| 41 | 3-pyridyl | H | 5 | dimethylamino-sulphonyl | 2 | 2 | CH₂ | 160–161 | Found: C, 58.88; H, 5.81; N, 12.93; $C_{21}H_{25}N_4O_4S$ requires: C, 58.58; H, 6.09; N, 13.02%. |
| 42 | 3-pyridyl | H | 5 | 3-methyl-butanoyl | 2 | 2 | CH₂ | 171–172.5 | Found: C, 71.03; H, 6.79; N, 10.27; $C_{24}H_{29}N_3O_3$ requires: C, 70.73; H, 7.17; N, 10.31%. |
| 43 | 3-pyridyl | H | 5 | cyclopropyl-acetyl | 2 | 2 | CH₂ | 159–161 | Found: C, 71.17; H, 6.72; N, 9.89; $C_{24}H_{27}N_3O_3$ requires: C, 71.08; H, 6.71; N, 10.36%. |
| 44 | 3-pyridyl | H | 4 | 4-fluorophenyl sulphonyl | 2 | 2 | CH₂ | 93–95 | Found: C, 62.20; H, 5.00; N, 8.76; $C_{25}H_{24}FN_3O_4S$ requires: C, 62.35; H, 5.02; N, 8.73%. |
| 45 | 3-pyridyl | H | 4 | dimethylamino sulphonyl | 2 | 2 | CH₂ | 179–181 | Found: C, 58.96; H, 6.00; N, 12.56; $C_{21}H_{26}N_4O_4S$ requires: C, 58.58; H, 6.09; N, 13.02%. |
| 46 | 3-pyridyl | H | 4 | 3-methyl-butanoyl | 2 | 2 | CH₂ | 195–196 | Found: C, 70.97; H, 7.11; N, 10.26; $C_{24}H_{29}N_3O_3$ requires: C, 70.73; H, 7.17; N, 10.31%. |
| 47 | 3-pyridyl | Me | 5 | 4-fluorophenyl sulphonyl | 2 | 2 | CH₂ | 197–199 | Found: C, 62.49; H, 5.07; N, 8.15; $C_{26}H_{26}FN_3O_4S$ requires: C, 63.01; H, 5.29; N, 8.48%. |
| 48 | 3-pyridyl | Me | 5 | 4-iodophenyl sulphonyl | 2 | 2 | CH₂ | 173–176 | Found: C, 52.02; H, 4.27; N, 6.81; $C_{26}H_{26}IN_3O_4S$ requires: C, 51.74; H, 4.34; N, 6.96%. |
| 49 | 3-pyridyl | Me | 5 | 4-trifluoro-methylphenyl-sulphonyl | 2 | 2 | CH₂ | 185–187 | Found: C, 59.51; H, 4.84; N, 7.53; $C_{27}H_{26}F_3NO_4S$ requires: C, 59.44; H, 4.80; N, 7.70%. |
| 50 | 3-pyridyl | Me | 4 | 4-fluorophenyl sulphonyl | 2 | 2 | CH₂ | 218–220 | Found: C, 63.07; H, 5.19; N, 8.38; $C_{26}H_{26}FN_3O_4S$ requires: C, 63.01; H, 5.29; N, 8.38%. |
| 51 | H | H | 5 | 4-chlorophenyl sulphonyl | 0 | 2 | direct link | 174–176 | Found: C, 54.29; H, 4.12; N, 7.16; $C_{17}H_{15}ClN_2O_4S$ requires: C, 53.90; H, 3.99; N, 7.39%. |
| 52 | H | H | 5 | 4-fluorophenyl sulphonyl | 0 | 2 | direct link | 140–141 | Found: C, 55.91; H, 4.08; N, 7.30; $C_{17}H_{15}FN_2O_4S$ requires: C, 56.33; H, 4.17; N, 7.73%. |

-continued

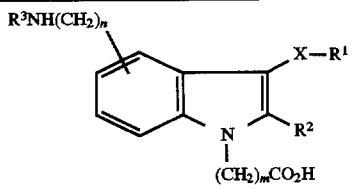

| Ex | R¹ | R² | R³NH(CH₂)ₙ position | R³ | n | m | x | m.p. °C. | Analytical Data |
|---|---|---|---|---|---|---|---|---|---|
| 53 | 4-fluoro-phenyl | H | 5 | phenyl-sulphonyl | 0 | 2 | $CH_2$ | 178–181 | Found: C, 63.37; H, 4.59; N, 5.90; $C_{24}H_{21}FN_2O_4S$ requires: C, 63.70; H, 4.68; N, 6.19%. |
| 54 | 4-fluoro-phenyl | H | 5 | 4-trifluoro-methylphenyl-sulphonyl | 0 | 2 | $CH_2$ | 171–175 | Found: C, 58.14; H, 3.61; N, 5.01; $C_{25}H_{20}F_4N_2O_4S$ requires: C, 57.69; H, 3.87; N, 5.38%. |
| 55 | 4-fluoro-phenyl | H | 5 | 4-methoxy-phenyl-sulphonyl | 0 | 2 | $CH_2$ | 166–168 | Found: C, 62.14; H, 4.73; N, 5.93; $C_{25}H_{23}FN_2O_5S$ requires: C, 62.23; H, 4.80; N, 5.81%. |
| 56 | 4-fluoro-phenyl | H | 5 | 4-methyl-phenyl-sulphonyl | 0 | 2 | $CH_2$ | 203–206 | Found: C, 64.12; H, 4.79; N, 5.95; $C_{25}H_{23}FN_2O_4S$ requires: C, 64.36; H, 4.97; N, 6.00%. |

EXAMPLE 57

1,2-Dimethyl-5-[(4-fluorophenyl)sulphonyl]amino-1H-indole-1-propanoic acid

A solution of 5-[(4-fluorophenyl)sulphonyl]amino-3-(1H-imidazol-1-ylmethyl)-2-methyl-1H-indole-1-propanoic acid (0.30 g) in ethanol (5 ml) and acetic acid (5 ml) was hydrogenated for 24 hours at 50° C. and 4.5 atm. in the presence of 10% palladium on carbon (30 mg). The mixture was filtered and the residue was washed with ethanol. The filtrate and washings were combined and evaporated, and the residue was partitioned between ethyl acetate and water. The organic layer was washed twice with water and dried ($MgSO_4$). The solvent was evaporated and the residue was chromatographed on silica gel, using dichloromethane/methanol (19:1) as eluant. The product fractions were combined and evaporated to give the title compound as a gum (0.035 g), Rf. 0.75(SS7). δ(DMSOd₆): 1.96(3H,s), 2.25(3H, s), ca 2.48(2H,t), 4.20(2H,t), 6.70(1H,d), 6.98(1H,s), 7.15 (1H,d), 7.26(2H,m), 7.66(2H,m), 9.71 (1H,s).

EXAMPLE 58

| Pharmaceutical Capsules | mg/capsule |
|---|---|
| Thromboxane A₂ Antagonist | 50.0 |
| Thromboxane Synthetase Inhibitor | 150.0 |
| Starch | 49.0 |
| Magnesium stereate BP | 1.0 |
| | 250 mg |

The thromboxane A₂ antagonist and the thromboxane synethase inhibitor are sieved and blended with the starch and the excipients. The mix is filled into size No. 2 hard gelatin capsules, using suitable machinery. Capsules of other strengths or with different ratios of active ingredients may be prepared in a similar manner.

Regarding toxicity, the compounds of Examples 33,41,42,46 and 49 have each been administered acutely to dogs at doses up to 10 mg/kg orally. No signs of toxicity were observed.

PREPARATION 1

3-(1H-Imidazol-1-ylmethyl)-5-nitro-1H-indole

A mixture of N,N-dimethyl-5-nitro-1H-indole-3-methanamine (*J.Med, Chem*, 9, 140,(1966)) (9.10 g) and imidazole (2.96 g) in xylene (120 ml) was heated under reflux for 2.5 hours and then cooled. The solid was filtered off, washed with ether and dried to give the title compound (9.40 g), m.p. 230°–232° C. (from ethyl acetate/methanol). Found: C,59.85; H,4.39; N,22.80. $C_{12}H_{10}N_4O_2$ requires: C,59.50; H,4.16; N,23.13%.

PREPARATION 2

3-(1H-Imidazol-1-ylmethyl)-2-methyl-5-nitro-1H-indole

Treatment of 2, N,N-trimethyl-5-nitro-1H-indole-3-methanamine (J.Org.Chem., 28,2921(1963)) (5.60 g) with imidazole (1.90 g) in xylene (100 ml) according to the method of Preparation 1 gave the title compound (5.50 g), m.p. 240°–242° C. Found: C,61.02; H,4.41; N,21.68. $C_{13}H_{12}N_4O_2$ requires: C,60.92; H,4.72; N,21.87%.

PREPARATION 3

5-Nitro-3-(3-pyridylmethyl)-1H-indole a) 3-(3-Pyridyl)propanal

Dimethylsulphoxide (18.9 ml) in dry dichloromethane (120 ml) was added over 20 minutes to a stirred solution of oxalyl chloride (11.55 ml) in dry dichloromethane (225 ml) at –70° C. The mixture was stirred at –70° C. for 10 minutes and then a solution of 3-(3-pyridyl)propanol (16.56 g) in dry dichloromethane (120 ml) was added with stirring over 20 minutes. Stirring was continued at –70° C. for a further 20 minutes and then triethylamine (50.55 ml) was added dropwise and the temperature was allowed to rise to room temperature. Water (200 ml) was added and the layers were separated. The organic layer was washed twice with water, dried ($MgSO_4$) and evaporated. The residue was distilled to give the title compound as an oil (8.80 g), b.p. 88°–92° C. @ 0.3 mm., Rf. 0.15 (SS2). δ(CDCl₃): 2.80(3H,t), 2.93(3H, t), 7.18–7.21 (1H,m), 7.50(1H,d), 8.40–8.45(2H,m), 9.80 (1H,s).

b) 3-(3-Pyridyl)propanal-4-nitrophenylhydrazone 3-(3-Pyridyl)propanal (8.50 g) was added to a stirred suspension of 4-nitrophenylhydrazine (9.62 g) in ether 150 ml. After a minute an orange-brown oil formed which solidified on further stirring. The solid was filtered off to give the title compound pure enough for further reaction (14.05 g), m.p. 146°–147° C. (from ethyl acetate/methanol). Found: C,62.12; H,5.02; N,20.36. $C_{14}H_{14}N_4O_2$ requires: C,62.21; H,5.22; N,20.73%.

c) 5-Nitro-3-(3-pyridylmethyl)-1H-indole

The above hydrazone (15 g) was added portionwise to a stirred mixture of polyphosphoric acid (60 g) and toluene (180 ml). The mixture was then heated at 110° C. with stirring for 1 hour and then cooled, poured into water and basified with concentrated aqueous ammonia solution. The aqueous layer was separated and extracted three times with ethyl acetate. The organic layers were combined, washed with water and dried (MgSO$_4$). The solvent was evaporated and the residue was chromatographed on silica gel. Elution with dichloromethane/methanol (40:1), gradually increasing the polarity to 25:1, gave the title compound (9.4 g), m.p. 154°–156° C. (from ethyl acetate). Found: C,66.68; H,4.19; N,16.61. $C_{14}H_{11}N_3O_2$ requires: C,66.39; H,4.38; N,16.59%.

PREPARATION 4

5-Nitro-3-(3-pyridyl)-1H-indole a) 3-(2-EZ-methoxyethenyl)pyridine

Phenyllithium (111 ml of 1.8M solution in ether) was added dropwise to a stirred suspension of (methoxymethyl) triphenylphosphonium chloride (68.6 g) in dry ether (600 ml) at –50° C. The mixture was stirred at –50° C. for 2 hours and then allowed to reach 0° C. over 30 minutes. 3-Pyridinecarboxaldehyde (10.70 g) was added dropwise with stirring, and the mixture was stirred at room temperature for 18 hours. An excess of ammonium chloride solution was then added and the layers were separated. The aqueous layer was separated and washed with ether, and the organic layers were combined and dried (MgSO$_4$). The solvent was evaporated and the residue was chromatographed on silica gel initially using ethyl acetate/hexane (1:4) as eluant. The polarity was gradually increased to ethyl acetate/hexane (1:1) to give the pure product as an oil (8.82 g) which was used directly in the next stage.

b) 3-Pyridineacetaldehyde-4-nitrophenylhydrazone

A solution of 3-(2-EZ-methoxyethenyl)pyridine (3.43 g) in ethanol (15 ml) and 2N hydrochloric acid (25 ml) was heated under reflux for 1 hour and then cooled. 4-nitrophenylhydrazine (3.89 g) was added portionwise with stirring to give a solution which deposited a yellow solid. The mixture was cooled in ice and the solid was filtered off, washed with isopropanol, ether and then dried to give the title compound (5.32 g), m.p. 212°–214° C. Found: C,53.54; H,4.51; N,19.00. $C_{13}H_{12}N_4O_2$ requires: C,53.34; H,4.48; N,19.14%.

5-Nitro-3-pyridyl-1H-indole

The above hydrazone (4.30 g) was added to ice-cooled concentrated sulphuric acid (43 ml) at such a rate that the temperature did not rise above 20° C. The mixture was stirred at room temperature for 1 hour and was then stirred at 30° C. for a further 1 hour. It was carefully poured into 500 ml of ice water and the solution was basified with concentrated aqueous ammonia solution with cooling. The mixture was extracted twice with ethyl acetate and the combined extracts were washed with water and dried (MgSO$_4$). The solvent was evaporated and the residue was chromatographed on silica gel. Elution with ethyl acetate followed by ethyl acetate/methanol (19:1) gave the title compound (1.25 g), m.p. >265° C. Found: C,65.34; H,3.41; N,17.69. $C_{13}H_{19}N_3O_2$ requires: C,65.26; H,3.79; N,17.57%.

PREPARATION 5

3-(4-Fluorophenylmethyl)-5-nitro-1H-indole a) 3-(4-Fluorophenyl)propanal

Di-isobutylaluminium hydride (75 ml of 1.0M solution in toluene) was added dropwise to a stirred solution of ethyl (4-fluorophenyl)-propanoate (*J.Org.Chem.*,31, 1524 (1966)) (11.84 g) in toluene (130 ml) at –70° C. The solution was stirred at –70° C. for 90 minutes, then ca 100 ml of 15% ammonium chloride solution was added dropwise and the temperature was allowed to reach room temperature. The organic layer was separated, dried (Na$_2$SO$_4$) and evaporated to give an oil which was chromatographed on silica gel. Elution with dichloromethane/hexane (3:1) gave the title compound as an oil (7.05 g), Rf. 0.7(SS1).

$\delta$(CDCl$_3$): 2.77(2H,t), 2.93(2H,t), 6.94–7.00(2H,m), 7.13–7.17(2H,m) 9.81(1H,s).

b) 3-(4-Fluorophenyl)propanal-4-nitrophenylhydrazone

A solution of 3-(4-fluorophenyl)propanal (7.0 g) in ether (50 ml) was added to a stirred suspension of 4-nitrophenylhydrazine (7.0 g) in ether (1 50 ml), followed by sufficient ethyl acetate to achieve a clear solution. The solution was filtered and evaporated and the residue was crystallised from ethyl acetate/hexane to give the title compound (5.48 g), m.p. 125°–127° C. Found: C,62.81; H,4.87; N,14.44. $C_{15}H_{14}FN_3O_2$ requires: C,62.71; H,4.91; N,14.63%.

Evaporation of the filtrate and trituration of the residue with hexane gave a further 5.39 g of title compound pure enough for further reaction.

c) 3-(4-Fluorophenylmethyl)-5-nitro-1H-indole

The above hydrazone (1 0.5 g) was added portionwise to a stirred mixture of polyphosphoric acid (45 g) and toluene (120 ml) at 40° C. The resulting mixture was stirred at 105°–110° C. for 75 minutes and then cooled. The toluene layer was decanted off and the residue was poured into water. The mixture was extracted twice with toluene and all the organic layers were combined, washed with water and dried (Na$_2$SO$_4$). Evaporation of the solvent gave a solid which was crystallised from ethyl acetate to give the title compound (2.20 g), m.p. 142°–144° C. Found: C,66.44; H,3.68; N,10.00. $C_{15}H_{11}FN_2O_2$ requires: C,66.66; H,4.10; N,10.37%.

PREPARATION 6

5-Bromo-3-(3-pyridylmethyl)-1H-indole

Methyl magnesium iodide (4.0 ml of 3M solution in ether) was added over 5 minutes to a stirred solution of 5-bromo-1H-in dole (1.96 g) in dry tetrahydrofuran (25 ml) at 2° C., the resulting suspension was stirred at room temperature for 45 minutes. Separately, a solution of 3-(chloromethyl) pyridine was prepared by partitioning 3-(chloromethyl) pyridine hydrochloride (1.97 g) between water and dichloromethane followed by dropwise addition of triethylamine with shaking until the pH of the aqueous layer was >7. The layers were separated and the aqueous layer was extracted with dichloromethane. The organic layers were combined, dried (MgSO$_4$) and evaporated to ca 25 ml. The solution was dried for a further 20 minutes by the addition of 3A molecular sieves. It was then added dropwise with stirring to the suspension of the indole Grignard reagent. The mixture was heated at 75° C. for 2 hours with stirring and then allowed to cool to room temperature. A solution of ammonium chloride (1.0 g) in water (30 ml) was added with stirring and the resulting mixture was extracted several times with ethyl acetate. The combined organic layers were washed with water, dried (MgSO$_4$) and evaporated. The residue was chromatographed on silica gel using dichloromethane/methanol (50:1) as eluent. Impurity was eluted first followed by pure product. The product fractions were combined and evaporated and the residue was crystallised from ether to give the title compound (0.798 g), m.p. 126°–128° C. Found: C,58.76; H,3.92; N,9.67. C$_{14}$H$_{11}$BrN$_2$ requires: C,58.55; H,3.86; N,9.76%.

PREPARATION 7

4-Bromo-3-(3-pyridylmethyl)-1H-indole

Treatment of 4-bromo-1H-indole (*J.Org.Chem.*, 48 2066 (1983)) (16.95 g) with methyl magnesium bromide (34.6 ml of 3M solution in ether) followed by a dichloromethane solution of 3-(chloromethyl)pyridine (prepared from 17.02 g of 3-(chloromethyl)pyridine hydrochloride) according to the method of Preparation 6 gave the title compound (7.80 g), m.p. 173°–174° C. Found: C,58.90; H,3.88; N,9.80. C$_{14}$H$_{11}$BrN$_2$ requires: C,58.55; H,3.86; N,9.76%.

PREPARATION 8

5-Bromo-2-methyl-3-(3-pyridylmethyl)-1H-indole

A solution of 5-bromo-2-methyl-1H-indole (*J. Chem. Soc.*, 1428 (1965)) (2.0 g) and 3-pyridinecarboxaldehyde (1.02 g) in dry dichloromethane (20 ml) was added dropwise over 10 minutes to a stirred solution of triethylsilane (3.30 g) in trifluoroacetic acid (20 ml) at 0° C. The solution was stirred at 0° C. for 30 minutes and then evaporated under vacuum, keeping the temperature below 35° C. The residue was dissolved in dichloromethane, and the solution was washed with 2N sodium hydroxide, water and dried (MgSO$_4$). The solution was evaporated and the residue was chromatographed on silica gel, using dichloromethane/methanol (50:1) as eluent. The product fractions were combined and evaporated, and the residue was crystallised from ether to give the title compound (2.15 g), m.p. 188°–190° C. Found: C,59.62; H,4.43; N,9.26. C$_{15}$H$_{13}$BrN$_2$ requires: C,59.82; H,4.35; N,9.30%.

PREPARATION 9

4-Bromo-2-methyl-1H-indole and 6-bromo-2-methyl-1H-indole

3-Bromophenylhydrazine hydrochloride (26.5 g) was partitioned between ether and excess 2N sodium hydroxide solution. The ether layer was separated, washed with brine, dried (MgSO$_4$) and evaporated. The residue was redissolved in ether (25 ml) and the solution was cooled in ice. Acetone (25 ml) was added and the mixture was allowed to stand for 20 minutes and then evaporated. The residue was dissolved in acetone (25 ml), the solution was evaporated and the residue azeotroped with xylene. The residue was dissolved in xylene (30 ml) and the solution was added dropwise to stirred polyphosphoric acid (200 g) at 90° C. The mixture was stirred at 100° C. for 4 hours and then cooled and poured into ice water with stirring. The mixture was extracted twice with ether, and the combined extracts were washed with brine and dried (MgSO$_4$). The solvent was evaporated and the residue was chromatographed on silica gel using dichloromethane/hexane (1:4) as eluent. The product fractions were combined and evaporated, and the residue was crystallised twice from hexane to give 6-bromo-2-methyl-1H-indole (8.70 g), m.p. 132°–134° C. δ(CDCl$_3$): 2.38(3H, s), 6.15(1H,s), 7.12(1H,dd), 7.32(1H,d), 7.36(1H,d), 7.77 (1H,br).

The hexane filtrates were combined and evaporated, and the residue was chromatographed as before to give an oil (8.35 g) shown by nmr to consist of a mixture of 4-bromo-2-methyl-1H-indole and 6-bromo-2-methyl-1H-indole in the ratio 3:1.

δ(CDCl$_3$) for the 4-bromo isomer: 2.45(3H,s), 6.29(1H,s), 6.95(1H,dd), 7.21–7.27(2H,m), 7.96(1H,br).

PREPARATION 10

Benzyl (E)-3-(2-methyl-1H-indol-4-yl)-2-propenoate

A mixture of 4-bromo-2-methyl-1H-indole (containing 25% of the 6-bromo isomer) (8.30 g), palladium (II) acetate (0.45 g), tri-o-tolylphosphine (1.22 g), benzyl acrylate (9.76 g) and triethylamine (8.36 ml) in acetonitrile (8 ml) was heated in an oil bath at 140° C. under an atmosphere of nitrogen for 2 hours. The mixture was cooled and partitioned between dichloromethane and water. The organic layer was separated, washed three times with water and dried (MgSO$_4$). Evaporation of the solvent gave an oil which was chromatographed on silica gel. Elution with dichloromethane/hexane (1:1) first gave impurity followed by pure product. The product fractions were evaporated and the residue was triturated with ether to give the title compound (6.60 g), m.p. 135°–136° C. Found: C,77.98; H,6.10; N,4.71. C$_{19}$H$_{17}$NO$_2$ requires: C,78.33; H,5.88; N,4.81%. Further elution with dichloromethane/hexane (4:1) gave benzyl (E)-3-(2-methyl-1H-indol-6-yl)-2-propenoate (2.0 g), m.p. 164°–165° C. Found: C,78.53; H,6.06; N,4.74. C$_{19}$H$_{17}$NO$_2$ requires: C,78.33; H,5.88; N,4.81%.

The following compounds were prepared similarly.

| Structure | m.p. °C | Analytical Data |
|---|---|---|
| 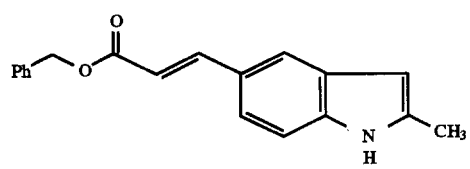 | 139–141 | Found: C, 77.74; H, 5.92; N, 4.52; C$_{19}$H$_{17}$NO$_2$ requires: C, 78.33; H, 5.88; N, 4.81%. |

| Structure | m.p. °C | Analytical Data |
|---|---|---|
| (CH₃)₃C-O-C(=O)-CH=CH-[indole with pyridylmethyl at 3-position, NH] | 160–161 | Found: C, 75.47; H, 6.46; N, 8.33; C₂₁H₂₂N₂O₂ requires: C, 75.42; H, 6.63; N, 8.38%. |
| (CH₃)₃C-O-C(=O)-CH=CH-[2-methylindole with pyridylmethyl at 3-position, NH] | 121–124 | Found: C, 75.53; H, 6.87; N, 8.12; C₂₂H₂₄N₂O₂ requires C, 75.83; H, 6.94; N, 8.04%. |
| O=C(OC(CH₃)₃)-CH=CH-[octahydroindole with pyridylmethyl, NH] | 146–148 | Found: C, 75.12; H, 6.40; N, 8.29; C₂₁H₂₂N₂O₂ requires: C, 75.42; H, 6.63; N, 8.38%. |

PREPARATION 11

Benzyl (E)-3-[2-methyl-3-(3-pyridylmethyl)-1H-indol-4-yl]-2-propenoate

A solution of benzyl (E)-3-[2-methyl-1H-indol-4-yl]-2-propenoate (4.75 g) and pyridine-3-carboxaldehyde (2.10 g) in dry dichloromethane (45 ml) was added dropwise to a stirred solution of triethylsilane (7.82 ml) in trifluoroacetic acid (40 ml) at 0° C. The solution was stirred, allowing the temperature to rise to room temperature, for 45 minutes and then evaporated. The residue was partitioned between dichloromethane and dilute aqueous ammonia solution. The aqueous layer was extracted with dichloromethane, and the combined organic layers were washed with water and dried (MgSO₄). The solvent was evaporated and the residue was chromatographed on silica gel. Elution with dichloromethane gave impurity, and further elution with dichloromethane/methanol (19:1) gave pure product. The product fractions were evaporated and the residue was triturated with ether to give the title compound (2.19 g), m.p. 180°–182° C., Rf. 0.35(SS1).

δ(CDCl₃): 2.43(3H,s), 4.21(2H,s), 5.21(2H,s), 6.30(1H, d), 7.01–7.11(2H,m), 7.28–7.42(8H,m), 8.19(1H,d), 8.22 (1H,s), 8.38(2H,s).

PREPARATION 12

Benzyl (E)-3-[3-(dimethylaminomethyl)-2-methyl-1H-indol-5-yl]-2-propenoate

Dimethylamine (3.35 ml of 33% solution in methylated spirit) was added to a stirred mixture of benzyl (E)-3-(2-methyl-1H-indol-5-yl)-2-propenoate (6.50 g) in a mixture of acetic acid (14 ml) and tetrahydrofuran (15 ml) at 0° C., followed by the dropwise addition of formaldehyde (1.75 ml of 40% aqueous solution). The mixture was stirred at room temperature for 3 hours and then diluted with ethyl acetate. 2N sodium hydroxide was added dropwise with stirring until the pH of the aqueous layer was ca.9. The mixture was filtered, and the residue was washed with water followed by ethyl acetate and then dried to give the title compound (6.58 g), m.p. 174°–177° C. Found: C,75.85; H,6.83; N,7.53. C₂₂H₂₄N₂O₂ requires: C,75.83; H,6.94; N,8.04%.

PREPARATION 13

Benzyl (E)-3-[3-(dimethylaminomethyl)-2-methyl-1H-indol-4-yl]-2-propenoate

Treatment of benzyl (E)-3-(2-methyl-1H-indol-4-yl)-2-propenoate (6.20 g) with dimethylamine (3.2 ml of 33% solution in methylated spirit), and formaldehyde (1.68 ml of 40% aqueous solution) in acetic acid (13 ml) and tetrahydrofuran (15 ml) according to the method of Preparation 12 gave the title compound as a foam (7.45 g), Rf. 0.3(SS3).

δ(CDCl₃): 2.25(6H,s), 2.37(3H,s), 3.49(2H,s), 5.28(2H, s), 6.48(1H,d) 7.07(1H,dd), 7.22–7.44(7H,m), 8.08(1H,s), 9.07(1H,d).

PREPARATION 14

Benzyl (E)-3-[3-(1H-imidazol-1-ylmethyl)-2-methyl-1H-indol-5-yl]-2-propenoate

A mixture of benzyl (E)-3-[(3-dimethylaminomethyl)-2-methyl-1H-indol-5-yl]-2-propenoate (7.65 g) and imidazole (1.64 g) in dry dioxan (50 ml) was heated under reflux for 4 hours. The solution was cooled, filtered and evaporated. The residue was chromatographed on silica gel using dichloromethane/methanol (19:1) as eluent. Evaporation of the product fractions and trituration of the residue with ether gave the title compound (4.85 g), m.p. 120°–122° C. Found: C,74.43; H,5.70; N,11.25. C₂₃H₂₁N₃O₂ requires: C,74.37; H,5.70; N,11.32%.

PREPARATION 15

Benzyl (E)-3-[3-(1H-imidazol-1-ylmethyl)-2-methyl-1H-indol-4-yl]-2-propenoate

A mixture of benzyl (E)-3-[(3-dimethylaminomethyl)-2-methyl-1H-indol-4-yl]-2-propenoate (7.45 g), and imidazole (1.57 g) in xylene (50 ml) was heated under reflux for 6 hours and the solution was evaporated. The residue was chromatographed on silica gel using dichloromethane/methanol as eluent. Evaporation of the product fractions and trituration of the residue with ether gave the title compound (3.85 g), m.p. 207°–208.5° C. Found: C,74.48; H,5.64; N,11.31. $C_{23}H_{21}N_3O_2$ requires: C,74.37; H,5.70; N,11.32%.

PREPARATION 16

Methyl 5-nitro-3-(3-pyridylmethyl)-1H-indole-1-propanoate

Benzyltrimethylammonium hydroxide (0.8 ml of 40% solution in methanol) was added to a stirred mixture of 5-nitro-3-(3-pyridylmethyl)-1H-indole (7.34 g) and methyl acrylate (3.0 g) in dioxan (140 ml) and the resulting solution was stirred for 75 minutes and then evaporated. The residue was partitioned between water and ethyl acetate. The aqueous layer was separated and extracted with ethyl acetate. The organic layers were combined, washed with water and dried ($Na_2SO_4$). Evaporation of the solvent gave a solid which was crystallised from ethyl acetate/hexane to give the title compound (7.33 g), m.p. 101°–102° C. Found: C,63.85; H,4.86; N,12.37. $C_{18}H_{17}N_3O_4$ requires: C,63.71; H,5.05; N,12.38%.

The following compounds were prepared similarly.

dimethylformamide (10 ml) at room temperature, and the mixture was stirred for 30 minutes. Ethyl 4-bromobutanoate (0.40 g) was added and the mixture was stirred for 18 hours. Further sodium hydride (0.11 g of 60% dispersion) was added, the mixture was stirred for 30 minutes and then further ethyl 4-bromobutanoate (0.40 g) was added. Stirring was continued for an additional 4 hours and then the mixture was partitioned between ethyl acetate and water. The organic layer was separated, washed twice with water and dried ($MgSO_4$). The solvent was evaporated and the residue was chromatographed using dichloromethane/methanol (100:1) as eluent. The product fractions were combined and evaporated, and the residue was triturated with ether to give the title compound (0.51 g), m.p. 76°–78° C. Found: C,64.92; H,5.48; N,11.95. $C_{19}H_{19}N_3O_4$ requires: C,64.58; H,5.42; N,11.89%.

PREPARATION 18

Methyl 5-nitro-3-(3-pyridyl)-1H-indole-1-propanoate

Benzyltrimethylammonium hydroxide (0.17 ml of 40% solution in methanol) was added to a stirred suspension of 5-nitro-3-(3-pyridyl)-1H-indole (0.95 g) and methyl acrylate (0.41 g) in a mixture of tetrahydrofuran (10 ml) and dioxan (15 ml), and the mixture was stirred at room temperature for

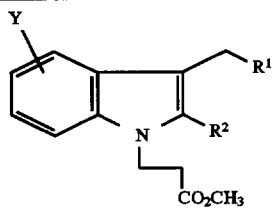

| $R^1$ | $R^2$ | Y | m.p. °C. | Analytical Data |
|---|---|---|---|---|
| 1-imidazolyl | H | 5-Nitro | 152–154 | Found: C, 58.88; H, 5.01; N, 17.07; $C_{16}H_{16}N_4O_4$ requires: C, 58.53; H, 4.91; N, 17.07%. |
| 1-imidazolyl | $CH_3$ | 5-Nitro | 150–151 | Found: C, 59.82; H, 5.28; N, 16.41; $C_{17}H_{18}N_4O_4$ requires: C, 59.64; H, 5.30; N, 16.37%. |
| 1-imidazolyl | $CH_3$ | 5-(E)-$PhCH_2O_2CCH$=CH— | 113–116 | Found: C, 70.97; H, 5.95; N, 9.12; $C_{12}H_{27}N_3O_4$ requires: C, 70.88; H, 5.95; N, 9.19%. |
| 1-imidazolyl | $CH_3$ | 4-(E)-$PhCH_2O_2CCH$=CH— | — | Found: C, 70.88; H, 5.90; N, 8.91; $C_{27}H_{27}N_3O_4$ requires: C, 70.88; H, 5.95; N, 9.19%. |
| 3-pyridyl | H | 5-(E)-t-$BuO_2CCH$=CH— | — | Found: C, 71.04; H, 6.67; N, 6.43; $C_{25}H_{28}N_2O_4$ requires: C, 71.40; H, 6.71; N, 6.66%. |
| 3-pyridyl | H | 4-(E)-t-$BuO_2CCH$=CH— | 86–88 | Found: C, 71.69; H, 6.59; N, 6.77; $C_{25}H_{28}N_2O_4$ requires: C, 71.40; H, 6.71; N, 6.66%. |
| 3-pyridyl | $CH_3$ | 5-(E)-t-$BuO_2CCH$=CH— | 91–93 | Found: C, 72.17; H, 6.96; N, 6.42; $C_{26}H_{30}N_2O_4$ requires: C, 71.86; H, 6.96; N, 6.45%. |
| 3-pyridyl | $CH_3$ | 4-(E)-t-$BuO_2CCH$=CH— | — | Found: C, 74.34; H, 6.07; N, 6.05; $C_{29}H_{28}N_2O_4$ requires: C, 74.37; H, 6.03; N, 5.98%. |

PREPARATION 17

Ethyl 5-nitro-3-(3-pyridyl)-1H-indole-1-butanoate

5-Nitro-3-(3-pyridyl)-1H-indole (0.60 g) was added portionwise to a stirred suspension of sodium hydride (0.11 g of 60% dispersion in mineral oil) in dry N,N-

2 hours. Methanol (10 ml) was added to give a clear solution followed by further methyl acrylate (0.41 g) and benzyltrimethylammonium hydroxide solution (0.17 ml) and stirring was continued for an additional 18 hours. Potassium t-butoxide (100 mg) was added and stirring was continued for a further 6 hours and the solution was evaporated. The residue was partitioned between ethyl acetate and water and the organic layer was separated and dried (MgSO,). Evaporation of the solvent gave a solid which was crystallised from dichloromethane/hexane to give the title compound (0.48 g), m.p. 123°–125° C. Found: C,62.85H,4.62; N,12.91. $C_{17}H_{15}N_3O_4$ requires: C,62.76; H,4.65; N,12.92%.

PREPARATION 19

Methyl 3-(4-fluorophenylmethyl)-5-nitro-1H-indole-1-propanoate

Tetrabutylammonium bromide (0.262 g) and potassium t-butoxide (100 mg) were added to a stirred solution of 3-(4-fluorophenylmethyl)-5-nitro-1H-indole (2.20 g) and methyl acrylate (0.84 g) in dioxan (30 ml) and the solution was stirred at room temperature for 66 hours. Further quantities of methyl acrylate (0.5 g), tetrabutylammonium bromide (262 mg) and potassium t-butoxide (100 mg) were added and stirring was continued for an additional 5 hours. The solution was poured into water and the mixture was extracted twice with ether. The combined ether extracts were washed with water, dried ($Na_2SO_4$) and evaporated. The residue was chromatographed on silica gel using hexane/ dichloromethane (1:4) as eluent. The product fractions were combined and evaporated to give the title compound as a gum (1.90 g). Found: C,64.43; H,4.39; N,7.65. $C_{19}H_{17}FN_2O_4$ requires: C,64.03; H,4.81; N,7.86%.

PREPARATION 20

Methyl 5-nitro-1H-indole-1-propanoate

Reaction of 5-nitro indole (3.0 g) with methyl acrylate (2.29 g) in the presence of potassium t-butoxide (0.258 g) and tetrabutylammonium bromide according to the method of Preparation 19 gave the title compound (3.0 g), m.p. 97°–99° C. Found: C,57.86; H,4.84; N,10.78. $C_{12}H_{12}N_2O_4$ requires: C,58.06; H,4.87; N,11.28%.

PREPARATION 21

Methyl 5-(2-carboxyethyl)-3-(1H-imidazol-1-ylmethyl)-2-methyl-1H-indole-1-propanoate A solution of benzyl (E)-3-[3-(1H-imidazol-1-ylmethyl)-1-(2-methoxycarbonylethyl)-2-methyl-1H-indol-5-yl]-2-propenoate (2.0 g) in tetrahydrofuran (40 ml) was hydrogenated at room temperature and 4.5 atm. in the presence of 10% palladium on carbon (0.20 g) until reaction was complete (5 hours). The mixture was filtered and the residue was washed with ethyl acetate. The combined filtrate and washings were evaporated and the residue was triturated with ether to give the title compound (1.52 g), m.p. 134°–137° C. Found: C,65.31; H,6.35; N,10.70. $C_{20}H_{23}N_3O_4$ requires: C,65.02; H,6.28N,11.38%.

PREPARATION 22

Methyl 4-(2-carboxyethyl)-3-(1H-imidazol-1-ylmethyl)-2-methyl-1H-indole-1-propanoate Hydrogenation of benzyl (E)-3-[3-(1H-imidazol-1-ylmethyl)-1-(2-methoxycarbonylethyl)-2-methyl-1H-indol-4-yl]-2-propenoate (1.40 g) in the presence of 10% palladium on carbon (0.15 g) according to the method of Preparation 21 gave the title compound (0.82 g), m.p. 136°–138° C.

δ($DMSOd_6$): 2.34(2H,t), 2.57(3H,s), 2.74(2H,t), 2.96(2H, t), 3.54(3H,s), 4.40(2H,t), 5.32(2H,s), 6.78(1H,d), 6.82(1H, s), 6.90(1H,s), 6.98(1H,dd), 7.29(1H,d), 7.43(1H,s).

PREPARATION 23 t-Butyl 1-(2-methoxycarbonylethyl)-3-(3-pyridylmethyl)-1H-indole-5propanoate

A mixture of t-butyl (E)-3-[1-(2-methoxycarbonylethyl)-3-(3-pyridylmethyl)-1H-indol-5-yl]-2-propenoate (7.86 g), 10% palladium on carbon (0.70 g) and ammonium formate (5.60 g) in a mixture of methanol (40 ml) and tetrahydrofuran (40 ml) was heated at 60° C. for 3 hours and then cooled. The mixture was filtered and the residue was washed with methanol. The filtrate and washings were combined and evaporated, and the residue-was partitioned between water and ether. The organic layer was separated and the aqueous layer was extracted with ether. The organic layers were combined, washed with water and dried ($MgSO_4$). Evaporation of the solvent gave the title compound as an oil (7.80 g). Found: C,70.51; H,6.98; N,6.54. $C_{25}H_{30}N_2O_4$ requires: C,71.06; H,7.16; N,6.63%.

PREPARATION 24 t-Butyl 1-(2-methoxycarbonylethyl)-3-(3-pyridylmethyl)-1H-indole-4-propanoate

Treatment of t-butyl (E)-3-[1-(2-methoxycarbonylethyl)-3-(3-pyridylmethyl)-1H-indole-4-yl]-2-propenoate (5.15 g) with 10% palladium on carbon (0.50 g) and ammonium formate (7.71 g) according to the method of Preparation 23 gave the title compound, (4.67 g) m.p. 80°–82° C. Found: C,71.43; H,7.06; N,6.35. $C_{25}H_{30}N_2O_4$ requires: C,71.06; H,7.16; N,6.63%.

PREPARATION 25

Methyl 5-(2-carboxyethyl)-3-(3-pyridylmethyl)-1H-indole-1-propanoate

Trifluoroacetic acid (15 ml) was added to a stirred solution of t-butyl 1-(2-methoxycarbonylethyl)-3-(3-pyridylmethyl)-1H-indole-5-propanoate (7.60 g) in dry dichloromethane (100 ml) at room temperature, and stirring was continued for 18 hours. The solution was evaporated and the residue was azeotroped with toluene and then dissolved in ethyl acetate. Saturated sodium bicarbonate solution was added slowly with shaking until the pH of the aqueous layer was 4–5. The organic layer was then separated, washed with water and dried ($MgSO_4$). The solvent was evaporated and the residue was triturated with ether to give the title compound (5.70 g), m.p. 108°–110° C. Found: C,68.80; H,6.16; N,7.57%. $C_{21}H_{22}N_2O_4$ requires: C,68.83; H,6.05; N,7.65%.

The following compounds were prepared similarly from the corresponding t-butyl ester.

| Structure | m.p. °C | Analytical Data |
|---|---|---|
| [structure: indole with HO2C-CH2CH2 at 4-position, 3-pyridylmethyl at 3-position, N-CH2CH2-CO2CH3] | 199–201 | Found: C, 68.65; H, 6.27; N, 7.53. C$_{21}$H$_{22}$N$_2$O$_4$ requires: C, 68.83; H, 6.05; N, 7.65%. |
| [structure: indole with HO2C-CH=CH- at 5-position, 2-methyl, 3-(3-pyridylmethyl), N-CH2CH2-CO2CH3] | 180–182 | Found: C, 69.65; H, 5.73; N, 7.19. C$_{22}$H$_{22}$N$_2$O$_4$ requires: C, 67.82; H, 5.86; N, 7.40%. |

PREPARATION 26

Methyl 5-(2-carboxyethyl)-2-methyl-3-(3-pyridylmethyl)-1H-indole-1-propanoate

A mixture of (E)-3-[1-(2-methoxycarbonylethyl)-2-methyl-3-(3-pyridylmethyl)-1H-indol-5-yl]-2-propenoic acid (2.02 g), 10% palladium on carbon (0.20 g) and ammonium formate (1.68 g) in methanol (20 ml) and tetrahydrofuran (20 ml) was heated at 60° C. for 4 hours and then cooled and filtered. The residue was washed with methanol, and the filtrate and washings were combined and evaporated. The residue was triturated with dilute acetic acid to give a gummy solid. The solid was filtered off and boiled with ether to give the title compound as a crystalline solid (1.79 g), m.p. 144°–146° C. Found: C,69.60; H,6.20; N,7.16. C$_{22}$H$_{24}$N$_2$O$_4$ requires: C,69.45; H,6.36; N,7.37%.

PREPARATION 27

Methyl 4-(2-carboxyethyl)-2-methyl-3-(3-pyridylmethyl)-1H-indole-1-propanoate

Treatment of benzyl 1-(2-methoxycarbonylethyl)-2-methyl-3-(3-pyridylmethyl)-1H-indole-1-propanoate (6.45 g) with palladium on carbon (0.65 g) and ammonium formate (8.90 g) according to the method of Preparation 26 gave the title compound (3.76 g). m.p. 165°–167° C. Found: C,69.43; H,6.42; N,7.37. C$_{22}$H$_{24}$N$_2$O$_4$ requires: C,69.45; H,6.36; N,7.37%.

PREPARATION 28

Methyl 5-(2-benzyloxycarbonylaminoethyl)-3-(1H-imidazol-1-ylmethyl)-2-methyl-1H-indole-1-propanoate Diphenylphosphoryl azide (0.744 g) was added to a mixture of methyl 5-(2-carboxyethyl)-3-(1H-imidazol-1-ylmethyl)-2-methyl-1H-indole-1-propanoate (1.0 g) and triethylamine (0.274 g) in dry dioxan (5 ml) at 50° C. The solution was then heated at 100° C. for 1 hour to give a clear solution. Benzyl alcohol (0.352 g) was added and the solution was heated at 1000° C. for a further 20 hours and then evaporated. The residue was partitioned between ethyl acetate and sodium bicarbonate solution. The organic layer was separated, washed with brine and dried (MgSO$_4$). The solvent was evaporated and the residue was chromatographed on silica gel using dichloromethane/methanol (97:3) as eluent. The product fractions were combined and evaporated to give the title compound as a gum (0.41 g). Found: C,68.12; H,6.41; N,11.23. C$_{27}$H$_{30}$N$_4$O$_4$ requires: C,68.33; H,6.37; N,11.81%.

The following compounds were prepared similarly using either benzyl alcohol or t-butanol.

| Structure | m.p. °C | Analytical Data |
|---|---|---|
| [structure: (CH$_3$)$_3$CO-C(O)-NH-CH2CH2- on indole 5-position, 3-(3-pyridylmethyl), N-CH2CH2-CO2CH3] | Gum | Rf. 0.4(SS4). δ(CDCl$_3$): 1.46(9H, s), 2.82(2H, t), 2.89(2H, t), 3.42(2H, m), 3.67(3H, s), 4.08(2H, s), 4.41(2H, t), 4.58(1H, br), 6.84(1H, s), 7.08(1H, d), 7.22(1H, m), 7.28–7.32(2H, m), 7.55(1H, d), 8.47(1H, d), 8.59(1H, s). |

| Structure | m.p. °C. | Analytical Data |
|---|---|---|
| (Structure: (CH₃)₃CO-C(=O)-NH-CH₂CH₂-[indole with 3-pyridylmethyl at 3-position and N-CH₂CH₂-CO₂CH₃]) | Gum | Rf. 0.5(SS3).<br>δ(CDCl₃): 1.44(9H, s), 2.80(2H, t),<br>2.99(2H, t), 3.32(2H, m), 2.65(3H, s),<br>4.15(2H, s), 4.38(2H, t), 4.57(1H, br),<br>6.75(1H, s), 6.87(1H, d), 7.16–7.22(3H, m),<br>7.45(1H, d), 8.44(1H, d), 8.50(1H, s). |
| (Structure: C₆H₅-O-C(=O)-NH-CH₂CH₂-[indole with imidazolylmethyl at 3-position, 2-CH₃, and N-CH₂CH₂-CO₂CH₃]) | 127.5–129.5 | Found: C, 68.15; H, 6.42; N, 11.77.<br>C₂₇H₃₀N₄O₄ requires: C, 68.33; H, 6.37; N, 11.81%. |

PREPARATION 29

Methyl 5-(2-t-butoxycarbonylaminoethyl)-2-methyl-3-(3-pyridylmethyl)-1H-indole-1-propanoate Diphenylphosphoryl azide (3.99 g) was added to a stirred mixture of methyl 5-(2-carboxyethyl)-2-methyl-3-(3-pyridylmethyl)-1H-indole-1-propanoate (5.00 g) and triethylamine (1.46 g) in dry t-butanol (30 ml) and the mixture was heated at 100° C. for 18 hours and then evaporated. The residue was dissolved in dichloromethane, and the solution was washed twice with water and dried (MgSO₄). The solvent was evaporated and the residue was chromatographed on silica gel. Elution with dichloromethane and evaporation of the product fractions gave the title compound as a gum (4.51 g), Rf. 0.35(SS4). δ(CDCl₃): 1.42(9H,s), 2.37(3H,s), 2.73(2H,t), 2.82(2H,t), 3.36(2H,m), 3.68(3H,s), 4.05(2H,s), 4.39(2H,t), 4.50(1H,br), 7.00(1H,d), 7.10–7.25 (3H,m) 7.41 (1H,d), 8.39(1H,d), 8.50(1H,s).

PREPARATION 30

Methyl 4-(2-t-butoxycarbonylaminoethyl)-2-methyl-3-(3-pyridylmethyl)-1H-indole-1-propanoate Treatment of methyl 4-(2-carboxyethyl)-2-methyl-3-(3-pyridylmethyl)-1H-indole-1-propanoate (3.70 g) with diphenylphosphoryl azide (2.95 g), triethylamine (1.08 g), and t-butanol (30 ml) as described in Preparation 29 gave the title compound as an oil (3.46 g), Rf. 0.5 (SS2). δ(CDCl₃): 1.44(9H,s), 2.37(3H,s), 2.77(2H,t), 2.87(2H,t), 3.23(2H,m), 3.68(3H,s), 4.28(2H,s), 4.45(2H,t), 4.53(1H,br), 6.82(1H,d), 7.10–7.13(2H,m), 7.21(1H,d), 7.29(1H,d), 8.38–8.42(2H, m).

PREPARATION 31

Methyl 5-amino-3-(3-pyridylmethyl)-1H-indole-1-propanoate

A mixture of methyl 5-nitro-3-(3-pyridylmethyl)-1H-indole-1-propanoate (1.20 g) and 10% palladium on carbon (120 mg) in methanol (75 ml) was hydrogenated at 50° C. and 4.5 atm. until reduction was complete (2 hours). The mixture was filtered and the catalyst was washed well with methanol. The filtrate and washings were combined and evaporated to give the title compound as an oil (1.05 g), Rf. 0.2(SS2). δ(CDCl₃): 2.76(2H,t), 3.45(2H,br), 3.63(3H,s), 3.98(2H,s), 4.32(2H,t), 6.66–6.68(1H,dd), 6.72(1H,d), 6.77 (1H,s), 7.11(1H,d), 7.14–7.18(1H,m), 7.48–7.51(1H,m), 8.42–8.44(1H,m), 8.56(1H,d).

The following compounds were prepared similarly as oils.

(General structure: 5-H₂N-indole with X–R¹ at 3-position, R² at 2-position, and N-(CH₂)ₘ-CO₂R⁷)

| R¹ | X | R² | m | R⁷ | Analytical Data |
|---|---|---|---|---|---|
| 1-imidazolyl | CH₂ | H | 2 | CH₃ | Rf. 0.7(SS5).<br>δ(CDCl₃): 2.83(2H, t), 3.47(2H, br), 3.67(3H, s)<br>4.38(2H, t), 5.19(2H, s), 6.68(1H, d), 6.71–6.74(1H, dd),<br>6.96(1H, s), 7.06(1H+1H, s), 7.15(1H, d), 7.59(1H, s). |

-continued

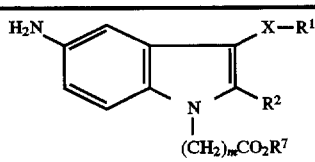

| R¹ | X | R² | m | R⁷ | Analytical Data |
|---|---|---|---|---|---|
| 1-imidazolyl | CH₂ | CH₃ | 2 | CH₃ | Rf. 0.4(SS2).<br>δ(CDCl₃): 2.42(3H, s), 2.77(2H, t), 3.50(2H, br), 3.68(3H, s), 4.39(2H, t), 5.16(2H, s), 6.63–6.69(2H, m), 6.93(1H, s), 7.05(1H, s), 7.14(1H, d), 7.54(1H, s). |
| 4-fluorophenyl | CH₂ | H | 2 | CH₃ | Rf. 0.4(SS6).<br>δ(CDCl₃): 2.77(2H, t), 3.42(2H, br), 3.65(1H, s), 3.97(1H, s), 4.33(2H, t), 6.67(1H, dd), 6.68–6.69(2H, d+s), 6.95(2H, t), 7.12(1H, d), 7.17–7.22(2H, m). |
| 3-pyridyl | direct link | H | 2 | CH₃ | Rf. 0.2(SS2).<br>δ(CDCl₃): 2.85(2H, t), 3.65(2H, br), 3.67(3H, s), 4.44(2H, t), 6.75(1H, dd), 7.18(1H, d), 7.27(1H, s), 7.27(1H, d), 7.30–7.34(1H, m), 7.87(1H, m), 8.47(1H, dd), 8.86(d). |
| 3-pyridyl | direct link | H | 3 | C₂H₅ | Rf. 0.2(SS2).<br>δ(CDCl₃): 1.24(3H, t), 2.15(2H, m), 2.32(2H, t), 3.45(2H, br), 4.11(2H, t), 4.19(2H, t), 7.18–7.23(3H, m), 7.30–7.35(1H, m), 7.89(1H, m), 8.47(1H, dd), 8.86(1H, dd). |
| H | direct link | H | 2 | CH₃ | Rf. 0.25(SS6).<br>δ(CDCl₃): 2.80(2H, t), 3.35(2H, br), 3.67(2H, s), 4.39(2H, t), 6.30(1H, d), 6.68(1H, dd), 6.93(1H, d), 7.04(1H, d), 7.14(1H, d). |

PREPARATION 32

Methyl 5-(2-aminoethyl)-3-(1H-imidazol-1-ylmethyl)-2-methyl-1H-indole-1-propanoate A solution of methyl 5-(2-benzyloxycarbonylaminoethyl)-3-(1H-imidazol-1-ylmethyl)-2-methyl-1H-indole-1-propanoate (0.57 g) in tetrahydrofuran (50 ml) was hydrogenated at room temperature and 4.5 atm. pressure in the presence 10% palladium on carbon (50 mg) for 20 hours. The mixture was filtered and the residue was washed with methanol. The filtrate and washings were combined and evaporated to give a gum which was chromatographed on silica gel. Elution with dichloromethane/methanol (19:1) gave impurity, and then further elution with dichloromethane/methanol/0.880 ammonia solution (95:5:1) gave pure product. The product fractions were evaporated to give the title compound as a gum (0.325 g), Rf. 0.4 (SS3). The product was used directly for further reaction.

PREPARATION 33

Methyl 4-(2-aminoethyl)-3-(1H-imidazol-1-ylmethyl)-2-methyl-1H-indole-1-propanoate Hydrogenation of methyl 4-(2-benzyloxycarbonylaminoethyl)-3-(1H-imidazol-1-ylmethyl)-2-methyl-1H-indole-1-propanoate (0.50 g) in tetrahydrofuran (20 ml) in the presence of 10% palladium on carbon (100 mg+a further 50 mg quantities after 24 and 48 hours) for 72 hours, followed by work up as described for Preparation 32 gave the title compound as a gum (0.20 g), Rf. 0.15(SS3). δ(CDCl₃): 1.70(2H,br), 2.47(3H,s), 2.81(2H, t), 2.88(4H,s), 3.70(3H,s), 4.48(2H,t), 5.37(2H,s), 6.86(1H, s), 6.95(1H,d), 7.04(1H,s), 7.17(1H,m), 7.24(1H,d), 7.42 (1H,s).

PREPARATION 34

Methyl 5-(2-aminoethyl)-3-(3-pyridylmethyl)-1H-indole-1-propanoate

Trifluoroacetic acid (5 ml) was added to a stirred solution of methyl 5-(2-t-butoxycarbonylaminoethyl)-3-(3-pyridylmethyl)-1H-indole-1-propanoate (5.0 g) in dry dichloromethane (50 ml) and the solution was stirred for 3 hours. An additional 5 ml of trifluoroacetic acid was then added and stirring was continued for a further 2 hours. The solution was evaporated and the residue was partitioned between dichloromethane and dilute aqueous ammonia. The aqueous layer was separated and extracted with dichloromethane. The organic layers were combined and evaporated. Water (ca 50 ml) was added followed by sufficient acetic acid to adjust the pH to ca4. The solution was washed twice with ethyl acetate and then made basic with concentrated aqueous ammonia solution. The mixture was extracted twice with dichloromethane and the combined extracts were dried (MgSO₄) and evaporated to give the title compound as a gum (2.51 g), Rf. 0.15(SS3).
(CDCl₃): 1.39(2H,s), 2.80–2.86(4H,m), 2.98(2H,t), 3.67 (3H,s), 4.08(2H,s), 4.42(2H,t), 6.83(1H,s), 7.08(1H,d), 7.20 (1H,m), 7.27–7.29(2H,m), 7.54(1H,d), 8.45(1H,d), 8.59(1H, s).

The following compounds were prepared similarly.

| Structure | Analytical Data |
|---|---|
| 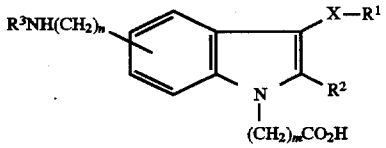 | Rf. 0.4(SS5).<br>δ(CDCl₃): 1.47(2H, s), 2.38(3H, s), 2.71–2.80(4H, m), 2.92(2H, t), 3.66(3H, s), 4.04(2H, s), 4.40(2H, t), 7.00(1H, d), 7.11(1H, m), 7.18(1H, s), 7.22(1H, d), 7.40(1H, d), 8.36(1H, d), 8.52(1H, s). |
| | Rf. 0.45(SS3).<br>δ(CDCl₃): 1.08(2H, br), 2.77(2H, t), 2.88–2.97(4H, m), 3.65(3H, s), 4.22(2H, s), 4.35(2H, t), 6.69(1H, s), 6.87(1H, d), 7.12–7.26(3H, m), 7.45(1H, d), 8.45(1H, d), 8.51(1H, s). |
| | Rf. 0.4(SS3).<br>δ(CDCl₃): 2.37(3H, s), 2.76(2H, t), 2.85(2H, t), 2.97(2H, t), 3.68(3H, s), 4.21(2H, s), 4.30(2H, br), 4.44(2H, t), 6.82(1H, d), 7.05–7.11(2H, m), 7.20(1H, d), 7.24–7.26(1H, m), 8.31(1H, d), 8.45(1H, s). |

We claim:

1. A compound of formula (I):

$$R^3NH(CH_2)_n\text{-indole-}X-R^1, R^2, (CH_2)_mCO_2H \quad (I)$$

or a pharmaceutically acceptable salt or biolabile ester thereof, wherein $R^1$ is $C_1$–$C_4$ alkyl, phenyl optionally substituted by up to three substituents independently selected from $C_1$–$C_4$ alkyl, $C_1$–$C_4$ alkoxy, halogen and $CF_3$, or is 1-imidazolyl, 3-pyridyl or 4-pyridyl;

$R^2$ is H or $C_1$–$C_4$ alkyl, $R^3$ is $SO_2R_4$ or $COR^4$ where $R^4$ is $C_1$–$C_4$ alkyl, $C_1$–$C_3$ perfluoroalkyl$(CH_2)_p$, $C_3$–$C_6$ cycloalkyl$(CH_2)_p$, aryl $(CH_2)_p$, furyl$(CH_2)_p$, thienyl$(CH_2)_p$ or pyridyl$(CH_2)_p$, p being 0, 1 or 2, or $R^4$ may be $NR^5R^8$ where $R^5$ is H or $C_1$–$C_4$ alkyl and $R^6$ is $C_1$–$C_6$ alkyl, $C_3$–$C_6$ cycloalkyl or aryl;

X is $CH_2$ or a direct link, with the proviso that when $R^1$ is 1-imidazolyl then X is $CH_2$;

m is 2, or 3;

n is 0, 1 or 2, and wherein the group $(CH_2)_nNHR^3$ is attached at the 5-position when n is 0 or 1, or at the 5- or 4-position when n is 2.

2. A compound, pharmaceutically acceptable salt or biolabile ester, according to claim 1, where $R^1$ is optionally substituted phenyl or pyridyl, $R^2$ is H, $R^3$ is $SO_2R^4$ where $R^4$ is optionally substituted phenyl, X is $CH_2$, m is 2, n is 0 or 2, and $(CH_2)_nNHR^3$ is attached at the 5-position.

3. A compound, pharmaceutically acceptable salt or biolabile ester, according to claim 1, where $R^1$ is pyridyl, $R^2$ is H, $R^3$ is $SO_2R^4$ where $R^4$ is optionally substituted phenyl or, $R^3$ is $COR^4$ where $R^4$ is alkyl, X is $CH_2$, m is 2, n is 2 and $(CH_2)_nNHR^3$ is attached at the 4-position.

4. A compound, pharmaceutically acceptable salt or biolabile ester, according to claim 1, where $R^1$ is 4-fluorophenyl, $R^3$ is arylsulphonyl, X is $CH_2$, m is 2, n is 0 and $(CH_2)_n$ $NHR^3$ is attached at the 5-position, or wherein $R^1$ is pyridyl, $R^3$ is 3-methylbutanoyl, X is $CH_2$, m is 2, n is 2 and $(CH_2)_nNHR^3$ is attached at the 4-position.

5. Any one of the following compounds, or pharmaceutically acceptable salts thereof, according to claim 1:

(i) methyl 5-[2-(4-fluorophenylsulphonyl)amino)ethyl]-3-(3-pyridylmethyl)-1H-indole-1-propanoate;

(ii) methyl 5-((4-fluorophenylsulphonyl)amino)-3-(1H-imidazol-1-ylmethyl)1H-indole-1-propanoate;

(iii) methyl 5-((4-fluorophenylsulphonyl)amino)-3-(1H-imidazol-1-ylmethyl)-2-methyl-1H-indole-1-propanoate;

(iv) methyl 5-((4-fluorophenylsulphonyl)amino)-3-(4-fluorophenylmethyl)-1H-indole-1-propanoate;

(v) methyl 5-((4-chlorophenylsulphonyl)amino)-3-(4-fluorophenylmethyl)- 1H-indole-1-propanoate;

(vi) methyl 5-((4-chlorophenylsulphonyl)amino)-3-(3-pyridyl)-1H-indole-1--propanoate;

(vii) ethyl 5-((4-chlorophenylsulphonyl)amino)-3-(3-pyridyl)-1H-indole-1-butanoate;

(viii) methyl 5-((4-fluorophenylsulphonyl)amino)-3-(3-pyridylmethyl)-1H-indole-1-propanoate;

(ix) methyl 5-((4-fluorophenylsulphonyl)amino)-3-(3-pyridylmethyl)-1H-indole-1-butanoate;

(x) methyl 5-[2-((4-fluorophenylsulphonyl)amino)ethyl]-3-(1H-imidazol-1-ylmethyl)-2-methyl-1H-indolepropanoate;

(xi) methyl 4-[2-((4-fluorophenylsulphonyl)amino)ethyl]-3-(1H-imidazol-1-ylmethyl)-2-methyl-1H-indolepropanoate;

(xii) methyl 5-[2-((4-fluorophenylsulphonyl)amino)ethyl]-3-(3-pyridylmethyl)-1H-indole-propanoate;

(xiii) methyl 5-[2-(dimethylaminosulphonyl)amino)ethyl]-3-(3-pyridylmethyl)-1H-indole-propanoate;

(xiv) methyl 5-[2-(3-methylbutanoylamino)ethyl]-3-(3-pyridylmethyl)-1H-indole-propanoate;

(xv) methyl 4-[2-((4-fluorophenylsulphonyl)amino)ethyl]-3-(3-pyridylmethyl)-1H-indole-propanoate;

(xvi) methyl 4-[2-((dimethylaminosulphonyl)amino)ethyl]-(3-pyridylmethyl)-1H-indole-propanoate;

(xvii) methyl 4-[2-((3-methylbutanoyl)amino)ethyl]-3-(3-pyridylmethyl)-1-H-indole-propanoate;

(xviii) methyl 5-[2-((4-fluorophenylsulphonyl)amino)ethyl]-3-(3-pyridylmethyl))-2-methyl-1H-indole-propanoate;

(xix) methyl 5-[2-((4-iodophenylsulphonyl)amino)ethyl]-3-(3-pyridylmethyl)2-methyl-1H-indole-propanoate;

(xx) methyl 5-[2-((4-trifluoromethylphenylsulphonyl)amino)-3-(3pyridylmethyl)-2-methyl-1H-indole-propanoate;

(xxi) methyl 4-[2-((4-fluorophenylsulphonyl)amino)ethyl]-3-(3-pyridylmethyl)2-methyl-1H-indole-propanoate;

(xxii) methyl 5-[4-chlorophenylsulphonyl)amino]-1H-indole-propanoate;

(xxiii) methyl 5-[4-fluorophenylsulphonyl)amino]-1H-indole-propanoate;

(xxiv) methyl 5-[(phenylsulphonyl)amino]-3-[(4-fluorophenyl)methyl]-1H-indole-propanoate;

(xxv) methyl 3-[(4-fluorophenyl)methyl]-5-[(4-trifuoromethylphenylsulphonyl)amino]-1H-indole-propanoate;

(xxvi) methyl 3-[(4-fluorophenyl)methyl]-5-[(4-methoxyphenylsulphonyl)amino]-1H-indole-propanoate;

(xxvii) methyl 3-[(4-fluorophenyl)methyl]-5-[(4-methylphenysulphonyl)amino]-1-H-indole propanoate.

(xxviii) methyl 5-[[(2-cyclopropyl)acetyl]amino]ethyl-3-(3-pyridylmethyl))1H-indole-1-propanoate;

(xxix) 5-[(4-Fluorophenyl)sulphonyl]amino-3-(3-pyridylmethyl)-1H-indole-1-propanoic acid;

(xxx) 5-[(4-fluorophenylsulphonyl)amino]-3-(1H-imidazol-1-ylmethyl)-1H-indole-1-propanoic acid;

(xxxi) 5-[(4-fluorophenylsulphonyl)amino]-3-(1H-imidazol-1-ylmethyl)-2-methyl-1H-indole-1-propanoic acid;

(xxxii) 5-[(4-fluorophenylsulphonyl)amino]-3-(4-fluorophenylmethyl)-1H-indole-1-propanoic acid;

(xxxiii) 5-[(4-chlorophenylsulphonyl)amino]-3-(4-fluorophenylmethyl)-1H-indole-1-propanoic acid;

(xxxiv) 5-((4-chlorophenylsulphonyl)amino]-3-(3-pyridyl)-1H-indole-1-propanoic acid;

(xxxv) 5-[(4-chlorophenylsulphonyl)amino]-3-(3-pyridyl)-1H-indole-1-butanoic acid;

(xxxvi) 5-[(4-fluorophenylsulphonyl)amino]-3-(3-pyridylmethyl)-1H-indole-1-butanoic acid;

(xxxvii) 5-[2-((4-fluorophenylsulphonyl)amino)ethyl]-3-(1H-imidazol-1-ylmethyl)-2-methyl-1H-indole-1-propanoic acid;

(xxxviii) 4-[2-((4-fluorophenylsulphonyl)amino)ethyl]-3-(1H-imidazol-1ylmethyl)-2-methyl-1H-indole-1-propanoic acid;

(xxxix) 5-[2-((4-fluorophenylsulphonyl)amino)ethyl]-3-(3-pyridylmethyl)-1H-indole-1-propanoic acid;

(xl) 5-[2-((methylsulphonyl)amino)ethyl]-3-(3-pyridylmethyl)-1H-indole-1-propanoic acid;

(xli) 5-[2-((dimethylaminosulphonyl)amino)]-3-(3-pyridylmethyl)-1H-indole-1-propanoic acid;

(xliii) 5-[2-((3-methylbutanoyl)amino)ethyl]-3-(3-pyridylmethyl)-1H-indole-1-propanoic acid;

(xliii) 5-[2-((cyclopropylacetyl)amino)ethyl]-3-(3-pyridylmethyl)-1H-indole-1-propanoic acid;

(xliv) 4-[2-((4-fluorophenylsulphonyl)amino)ethyl]-3-(3-pyridylmethyl)-1H-indole-1-propanoic acid;

(xlv) 5-[2-((dimethylaminosulphonyl)amino)ethyl]-3-(3-pyridylmethyl)-1H-indole-1-propanoic acid;

(xlvi) 5-[2-((3-methylbutanoyl)amino)ethyl]-3-(3-pyridylmethyl)-1H-indole-1-propanoic acid;

(xlvii) 5-[2-((4-fluorophenylsulphonyl)amino)ethyl]-3-(3-pyridylmethyl)-2-methyl-1H-indole-1-propanoic acid;

(xlviii) 5-[2-((4-iodophenylsulphonyl)amino)ethyl]-3-(3-pyridylmethyl)-2-methyl-1H-indole-1-propanoic acid;

(il) 5-[2-((4-trifluoromethylphenylsulphonyl)amino)ethyl]-3-(3pyridylmethyl)-2-methyl-1H-indole-1-propanoic acid;

(l) 4-[2-((4-fluorophenylsulphonyl)amino)ethyl]-3-(3-pyridylmethyl)-2methyl-1H-indole-1-propanoic acid;

(li) 5-[(4-chlorophenylsulphonyl)amino]-1H-indole-1-propanoic acid;

(lii) 5-[(4-fluorophenylsulphonyl)amino]-1H-indole-1-propanoic acid;

(liii) 3-(4-fluorophenyl)methyl-5[(phenylsulphonyl)amino]-1H-indole-1-propanoic acid;

(liv) 3-(4-fluorophenyl)methyl-5-[(4-trifluoromethylphenylsulphonyl)amino]-1H-indole-1-propanoic acid;

(lv) 3-(4-fluorophenyl)methyl-5[(4-methoxyphenylsulphonyl)amino]-1H-indole-1-propanoic acid;

(lvi) 3-(4-fluorophenyl)methyl-5-[(4-methylphenylsulphonyl)amino]-1H-indole-1-propanoic acid and;

(lvii) 5-[(4-fluorophenyl)sulphonyl]amino-2,3-dimethyl-1 H-indole-1propanoic acid.

6. A compound, salt or ester according to claim 1, which is radiolabelled.

7. A biolabile ester of a carboxylic acid compound of the formula (I) as claimed in claim 1, wherein said biolabile ester is a lower alkyl ester having from one to four carbon atoms in the alkyl moiety ($C_1$–$C_4$ alkyl).

8. A pharmaceutical composition for treating or preventing diseases or disorders mediated by selectively antagonizing the effect of thromboxane $A_2$ or its precursor prostaglandin $H_2$ at the thromboxane receptor in a mammalian subject, comprising a compound of the formula (I), or a pharmaceutically acceptable salt or biolabile ester thereof, as claimed according to claim 1, together with a pharmaceutically acceptable diluent or carrier.

9. The method of treating or preventing disease or disorders mediated by selectively antagonizing the effect of thromboxane $A_2$ or its precursor prostaglandin $H_2$ at the thromboxane receptor in a mammalian subject, which comprises administering to said mammal a therapeutically-effective amount of a compound of the formula (I)), or a pharmaceutically acceptable salt or biolabile ester thereof, as claimed in claim 1.

* * * * *